US006858644B2

(12) United States Patent
Benigni et al.

(10) Patent No.: US 6,858,644 B2
(45) Date of Patent: Feb. 22, 2005

(54) PACLITAXEL SOLVATES

(75) Inventors: Daniel A. Benigni, Elbridge, NY (US); Jack Z. Gougoutas, Princeton, NJ (US); John D. DiMarco, East Brunswick, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 10/304,615

(22) Filed: Nov. 26, 2002

(65) Prior Publication Data

US 2003/0144344 A1 Jul. 31, 2003

Related U.S. Application Data

(60) Provisional application No. 60/334,896, filed on Nov. 30, 2001.

(51) Int. Cl.$^7$ .............................................. A61K 31/335
(52) U.S. Cl. ...................... 514/449; 549/510
(58) Field of Search .......................... 514/449; 549/510

(56) References Cited

U.S. PATENT DOCUMENTS

| 4,492,757 A | 1/1985 | Kato et al. |
| 4,526,718 A | 7/1985 | Ross et al. |
| 4,680,391 A | 7/1987 | Firestone et al. |
| 4,814,470 A | 3/1989 | Colin et al. |
| 4,857,653 A | 8/1989 | Colin et al. |
| 4,876,399 A | 10/1989 | Holton et al. |
| 4,924,011 A | 5/1990 | Denis et al. |
| 4,924,012 A | 5/1990 | Colin et al. |
| 4,942,184 A | 7/1990 | Haugwitz et al. |
| 4,943,528 A | 7/1990 | Nakamura et al. |
| 4,960,790 A | 10/1990 | Stella et al. |
| 5,015,744 A | 5/1991 | Holton |
| 5,053,507 A | 10/1991 | Moriuchi et al. |
| 5,059,699 A | 10/1991 | Kingston et al. |
| 5,136,060 A | 8/1992 | Holton |
| 5,175,315 A | 12/1992 | Holton |
| 5,227,400 A | 7/1993 | Holton et al. |
| 5,229,526 A | 7/1993 | Holton |
| 5,243,045 A | 9/1993 | Holton et al. |
| 5,248,796 A | 9/1993 | Chen et al. |
| 5,250,683 A | 10/1993 | Holton et al. |
| 5,254,580 A | 10/1993 | Chen et al. |
| 5,272,171 A | 12/1993 | Ueda et al. |
| 5,274,124 A | 12/1993 | Holton |
| 5,279,949 A | 1/1994 | Nair |
| 5,284,864 A | 2/1994 | Holton et al. |
| 5,294,637 A | 3/1994 | Chen et al. |
| 5,300,638 A | 4/1994 | Farina et al. |
| 5,380,916 A | 1/1995 | Rao |
| 5,384,399 A | 1/1995 | Holton |
| 5,430,160 A | 7/1995 | Holton |
| 5,451,392 A | 9/1995 | Strobel et al. |
| 5,466,834 A | 11/1995 | Holton |
| 5,475,120 A | 12/1995 | Rao |
| 5,478,736 A | 12/1995 | Nair |
| 5,516,676 A | 5/1996 | Hanson et al. |
| 5,523,219 A | 6/1996 | Hanson et al. |
| 5,532,363 A | 7/1996 | Holton |
| 5,539,103 A | 7/1996 | Holton |
| 5,574,156 A | 11/1996 | Holton |
| 5,646,176 A | 7/1997 | Golik et al. |
| 5,670,673 A | 9/1997 | Rao |
| 5,717,115 A | 2/1998 | Holton |
| 5,723,634 A | 3/1998 | Holton |
| 5,744,333 A | 4/1998 | Cociancich et al. |
| 5,760,219 A | 6/1998 | Holton et al. |
| 5,877,205 A * | 3/1999 | Andersson .................. 514/449 |
| 6,017,948 A * | 1/2000 | Rubinfeld et al. .......... 514/449 |
| 6,069,260 A | 5/2000 | Holton |
| 6,124,481 A | 9/2000 | Holton |
| 6,136,989 A | 10/2000 | Foo et al. |

FOREIGN PATENT DOCUMENTS

| EP | 1 349 357 | 4/1974 |
| EP | 0 023 097 | 8/1984 |
| EP | 0 146 900 | 7/1985 |
| EP | 0 253 738 | 1/1988 |
| EP | 0 253 739 | 1/1988 |
| EP | 0 336 840 | 10/1989 |
| EP | 0 336 841 | 10/1989 |
| EP | 0 247378 | 9/1990 |
| EP | 0 404 586 | 12/1990 |
| EP | 0 405 104 | 1/1991 |
| EP | 0 421 283 | 4/1991 |
| EP | 0 495 718 | 7/1992 |
| EP | 0 414 610 | 5/1993 |
| EP | 0 569 281 | 11/1993 |
| EP | 0 582 469 | 2/1994 |
| EP | 0 534 708 | 9/1995 |
| EP | 0 553 780 | 9/1995 |
| EP | 0 428 376 | 1/1996 |
| EP | 0 529 483 | 2/1996 |
| EP | 0 537 905 | 3/1996 |
| EP | 0 534 707 | 12/1996 |
| EP | 0 558 959 | 4/1997 |

(List continued on next page.)

OTHER PUBLICATIONS

Abdel–Magid, A. et al., "Metal–Assisted Aldol Condensation of Chiral α–Halogenated Imide Enolates: A Stereocontrolled Chiral Epoxide Synthesis", J. Am. Chem. Soc., vol. 108, pp. 4595–4602 (1986).

Arbuck, S.G. et al., et al., Chapter 14: "Taxol: Clinical Results and Current Issues in Development", Taxol: Science and Applications, CRC Press, Inc., publ., Suffness, M., ed., pp. 379–415 (1995).

Bartholomew, D. et al., "A Novel Rearrangement Reaction Conversion of 3–(chloromethyl)azetidin–2–ones to azetidine–3–caboxylic acid esters", Tetrahedron Letters, vol. 32, No. 36, pp. 4795–4798.

(List continued on next page.)

Primary Examiner—Amelia A. Owens
(74) Attorney, Agent, or Firm—Deanna L. Baxam

(57) ABSTRACT

Biologically active crystalline solvates of paclitaxel are precipitated using polar, aprotic, organic solvents. A pharmaceutical composition is also disclosed, as well as the preparation of the novel solvates and their uses as anti-tumor agents.

36 Claims, 8 Drawing Sheets

FOREIGN PATENT DOCUMENTS

| | | |
|---|---|---|
| EP | 0 400 971 | 7/1998 |
| EP | 0 604 910 | 6/2000 |
| EP | 0 552 041 | 8/2000 |
| EP | 0 717 041 | 8/2002 |
| EP | 0 534 709 | 1/2003 |
| NZ | 200155 | 8/1985 |
| WO | WO 90/10443 | 9/1990 |
| WO | WO 92/07842 | 5/1992 |
| WO | WO 92/09589 | 6/1992 |
| WO | WO 93/02065 | 2/1993 |
| WO | WO 93/06079 | 4/1993 |
| WO | WO 93/06094 | 4/1993 |
| WO | WO 97/09443 | 3/1997 |
| ZA | 919224 | 11/1991 |

OTHER PUBLICATIONS

Barton, D.H.R. et al., "Asymmetric Synthesis of 1,3,4–Trisubstituted and 3,4–Disubstituted 2–Azetidinones: Strategy Based on Use of D–Glucosamine as a Chiral Auxiliary in the Staudinger Reaction", J. Chem. Soc. Perkin Trans. 1, pp. 3211–3212 (1990).

Borer, B.C. et al., "An Asymmetric Synthesis of a 3–hydroxy–β–lactam by Ketene–Imine Cycloaddition: Utilization of Chiral Ketenes from Carbohydrates", Tetrahedron Letters, vol. 32, No. 8, pp. 1039–1040 (1991).

Borman, S., "New family of Taxol, Taxotere analogs developed", Chem. & Engineering News, pp. 36–37 (Apr. 12, 1993).

Bose, A.K. et al., "Studies on β–Lactams. XXXVI. Monocyclic Cis β–Lactams via Penams and Cephams", J. Org. Chem., vol. 39, No. 19, pp. 2877–2884 (1974).

Bose, A.K. et al., "Studies on Lactams. Part XVI. Stereochemistry of β–Lactam Formation", Tetrahedron Letters, No. 34, pp. 3167–3170 (1971).

Bose, A.K. et al., "Studies on Lactams —V: 3–azido–2–azetidinones", Tetrahedron, vol. 23, pp. 4769–4776 (1967).

Bose, A.K. et al., "Studies on the Mechanism of β–Lactam Formation", Tetrahedron Letters, No. 40, pp. 4091–4094 (1972).

Brieva, R. et al., "Chemoenzynmatic Synthesis of the C–13 Side Chain of Taxol: Optically–Active 3–Hydroxy–4–phenyl β–Lactam Derivatives", J. Org. Chem., vol. 58, pp. 1068–1075 (1993).

Burnett, D.A. et al., "Synthesis of 3–(1–Hydroxyethyl–2–azetidinones via Ester–Imine Condensations", J. Org. Chem., vol. 50, pp. 5120–5123 (1985).

Chan, W.R. et al., "Taxa–4(16), 11–diene–5α,9α, 10β, 13β–tetraol, a New Taxane Derivative from the Heartwood of Yew (*T. baccata L.*): X–Ray Analysis of a p–Bromobenzoate Derivative", Chemical Communications, No. 24, pp. 923–925 (1996).

Chen, S.–H. et al., "Taxol Structure–Activity Relationships: Synthesis and Biological Evaluation of 2–deoxytaxol", Tetrahedron Letters, vol. 34, No. 20, pp. 3205–3206 (1993).

Cooper, R.D.G. et al., "Chiral control of the Staudinger reaction", Pure & Appl. Chem., vol. 59, No. 3, pp. 485–492 (1987).

Cosslo, F.P. et al., "Triphenylphosphine Dibromide and Dimethylsulfide Dibromide as Versatile Reagents for Beta–Lactam Synthesis", Tetrahedron Letters, vol. 26, No. 25, pp. 3041–3044 (1985).

Della Casa, D.P. et al., "The Isolation of Seven New Taxane Derivatives from the Heartwood of Yew (*Taxus baccata* L.)", Chemical Communications, pp. 1282–1283 (1969).

Denis, J.–N. et al., "A Highly Efficient, Practical Approach to Natural Taxol", vol. 110, pp. 5917–5919 (1988).

Denis, J.–N. et al., "An Efficient, Enantioselective Synthesis of the Taxol Side Chain", vol. 51, pp. 46–50 (1986).

Denis, J.–N. et al., "An Improved Synthesis of the Taxol Side Chain and of RP 56976", J. Org. Chem., vol. 55, pp. 1957–1959 (1990).

Deutsch, H.M. et al., "Synthesis of Congeners and Prodrugs. 3. Water–Soluble Prodrugs of Taxol with Potent Antitumor Activity", vol. 32, pp. 788–792 (1989).

Dordick, J.S., "Designing Enzymes for Use in Organic Solvents", Biotechnol. Prog., vol. 8, pp. 259–267 (1992).

Ettotouati, L. et al., "Plantes de Nouvelle–Calédonie. 114. Taxanes isolés des feuilles d'*Austrotaxus spicata* Compton (Taxacées)", Bulletin de la Société Chimique de France, No. 4, pp. 749–755 (1988).

Evans, D.A. et al., "The Asymmetric Synthesis of β–Lactam Antibiotics—1. Application of Chiral Oxazolidones in the Staudinger Reaction", Tetrahedron Letters, vol. 26, No. 32, pp. 3783–3786 (1985).

Farina, V. et al., "The Chemistry of Taxanes: Unexpected Rearrangement of Baccatin III During Chemoselective Debenzoylation with $Bu_3SnOMe/LiCl$", Tetrahedron Letters, vol. 33, No. 28, pp. 3979–3982 (1992).

Fones, W.S., "The Isomers of the β–phenyserines", J. Biol. Chem., vol. 204, pp. 323–328 (1953).

Georg, G.I. et al., "An Improved Method for the Stereoselective Synthesis of β–Lactams from Carboxylic Acids adn Imines", Tetrahedron Letters, vol. 32, No. 5, pp. 581–584 (1991).

Georg, G.I. et al., "Asymmetric Synthesis of α–Alkylated α–Amino Acids: Azocane–2–Caboxylic Acids", Tetrahedron Letters, vol. 33, No. 1, pp. 17–20 (1992).

Georg, G.I. et al., "Asymmetric Synthesis of β–Lactams and N–benzoyl–3–phenylisoserines via the Staudinger Reaction", Tetahedron Letters, vol. 32, No. 37, pp. 3151–3154 (1991).

Georg, G.I. et al., "Novel Biologically Active Taxol Analogues: Baccatin III 13–(N–Chlorobenzoyl)–(2'R, 3'S)–3'–phenylisoserinate) and Baccatin III 13–(N–Benzoyl–(2'R, 3'S)–3'–(p–chlorophenyl)isoserinate)", Bioorganic & Medicinal Chemistry Letters, vol. 2, No. 4, pp. 295–298 (1992).

Georg, G.I. et al., Chapter 6: "Stereocontrolled Ketene–Imine Cycloaddition Reactions", The Organic Chemistry of β–Lactams, VCH Publishers, Inc., publ., Georg, G.I., ed., pp. 295–368 (1993).

Georg, G.I. et al., "Stereoselectively Syn Aldol Reaction of the Lithium Ester Enotate of Ethyl N,N–Dimethylglycine in the Presence of Triethylborane", vol. 32, No. 40, pp. 5521–5524 (1991).

Glänzer, B.I. et al., "Enantioselective Hydrolyses by Baker's Yeast—II. Esters of N–Acetyl Amino Acids", Tetrahedron, vol. 43, No. 4, pp. 771–778 (1987).

Gluchowski, C. et al., "Preparation of β–Lactams by the Condesation of Lithium Ester Enolates with Aryl Aldimines", J. Org. Chem., vol. 45, pp. 3413–3416 (1980).

Gou, D.-M. et al., "A Practical Chemoenzymatic Synthesis of the Taxol C–13 Side Chain N–Benzoyl–(2R, 3S)–3–phenylisoserine", J. Org. Chem., vol. 58, pp. 1287–1289 (1993).

Grant, J., ed., Hackh's Chemical Dictionary Fourth Edition, McGraw–Hill, Inc., publ., p. 62 (1969).

Greene, T.W. et al., Protective Groups in Organic Synthesis, Second Edition, John Wiley & Sons, Inc., publ., pp. 10–14 (table of contents, Ch. 2) (1991).

Guenard, D. et al., "Search for new anticancer substances", Chemical Abstracts, vol. 114, No. 94484h, p. 2 (1991).

Guéritte–Voegelein, F. et al., "Chemical Studies of 10–deacetyl Baccatin III, Hemisynthesis of Taxol Derivatives", Tetrahedron, vol. 42, No. 16, pp. 4451–4460 (1986).

Hart, D.J. et al., "Asymmetric Synthesis of β–Lactams and the Carbapenem Antibiotic (+)–PS–5", J. Am. Chem. Soc., vol. 108, pp. 6054–6056 (1986).

Hart, D.J. et al., "The Ester Enolate–Imine Condensation Route to β–Lactams", Chem. Rev., vol. 89, pp. 1447–1465 (1989).

Hills, M.J. et al., "Lipase from *Brassica napus* L. discriminates against cis–4 and cis–6 unsaturated fatty acids and secondary and tertiary alcohols", Biochimica et Biophysica Acta, vol. 1042, pp. 237–240 (1990).

Hoenig, H. et al., "Chemoenzymic syntheses of enantiomerically pure hydroxy amino acids", Chemical Abstracts, vol. 115, No. 183831g, p. 985 (1991).

Holmes, F.A. et al., Chapter 3; "Current Status of Clinical Trials with Paclitaxel and Docetaxel", Taxane Anticancer Agents: Basic Science and Current Status, ACS Symposium Series, vol. 583, American Chemical Society, publ., Georg, G.I. et al., eds., pp. 31–57 (1995).

Holton, R.A. et al., "A synthesis of taxusin", Chemical Abstracts, vol. 109, No. 129360r, p. 726 (1988).

Holton, R.A. et al., "A Synthesis of Taxusin", J. Am. Chem. Soc., vol. 110, pp. 6558–6560 (1988).

Holton, R.A., "Synthesis of the Taxane Ring System", J. Am. Chem. Soc., vol. 106, pp. 5731–5732 (1984).

Hönig, H. et al., "Chemo–Enzymetic Synthesis of All Isometric 3–Phenylserines and –Isoserines", Tetrahedron, vol. 46, No. 11, pp. 3841–3850 (1990).

Hönig, H. et al., "Chemoenzymatic syntheses of enantiomerically pure hydroxy amino acids", Amino Acids: Chem. Biol. Med., pp. 134–142 (1989).

Hönig, H. et al., "Simultaneous Separation of Enantiomers of Diastereomers by Lipases", Tetrahedron Letters, vol. 31, No. 21, pp. 3011–3012 (1990).

Iriuchijima, S. et al., "Asymmetric Hydrolysis of (±)–α–Substituted Carboxylic Acid Esters with Microorganisms", Agric. Biol. Chem., vol. 45, No. 6, pp. 1389–1392 (1981).

Jones, J.B., "Enzymes in Organic Synthesis", Tetrahedron, vol. 42, No. 13, pp. 3351–3403 (1986).

Kaiser, E.M. et al., "Synthesis of Esters of Acid–Unstable Alcohols by Means of n–Butyllithium", The Journal of Organic Chemistry, vol. 35, No. 4, pp. 1198–1199 (1970).

Kato, Y. et al., "Enzyme–Mediated Asymmetric Hydrolysis of α–benzyloxycarboxylic esters", Tetrahedron Letters, vol. 28, No. 12, pp. 1303–1306 (1987).

Katritzky, A.R. et al., Handbook of Heterocyclic Chemistry, Second Edition 2000, Elsevier Science Ltd., publ., pp. 173–174 (2000).

Kingston, D.G.I. et al., "New Taxanes from *Taxus Brevifolia*", Journal of Natural Products, vol. 45, No. 4, pp. 466–470 (1982).

Klein, L.L., "Synthesis of 9–Dihydrotaxol: A Novel Bioactive Taxane", Tetrahedron Letters, vol. 34, No. 13, pp. 2047–2050 (1993).

Langrand, G. et al., "Lipase Catalyzed Reactions and Strategy for Alcohol Resolution", Tetrahedron Letters, vol. 27, No. 1, pp. 29–32 (1986).

Laschat, S. et al., "Carbohydrates as Chiral Templates: Stereoselective Synthesis of (R)–Homoallyl Amines Using L–Fucose as the Auxiliary Formally Enantiomeric to D–Galactose", Synlett, pp. 629–630 (1990).

Lewis, Sr., R.J., rev., Hawley's Condensed Chemical Dictionary, Twelfth Edition, Van Nostrand Reinhold, publ., pp. 21–22 (1993).

Lewis, Sr., R.J., rev., Hawley's Condensed Chemical Dictionary, Twelfth Edition, Van Nostrand Reinhold, publ., pp. 851–852 (1993).

Liu, C.L. et al., "Constituents of the Hearthwood of Taiwan Yew", Tai'wan Ko'hsueh, vol. 38, pp. 119–125 (1984).

Magri, N.F. et al., "Modified Taxols. 3. Preparation and Acylation of Baccatin III", J. Org. Chem., vol. 51, pp. 3239–3242 (1986).

Magri, N.F. et al., "Modified Taxols. 4. Synthesis and Biological Activity of Taxols Modified in the Side Chain", Journal of Natural Products, vol. 51, No. 2, pp. 298–306 (1988).

Mangata, L. et al., "Application of the vicinal hydroxyamination reaction with asymmetric induction to the hemisynthesis of taxol and analogs", Chemical Abstracts, vol. 112, No. 119169h, p. 774 (1990).

March, J., Advanced Organic Chemistry: Reactions, Mechanisms, and Structures, Fourth Edition, John Wiley & Sons, Inc., p. 351 (1992).

Mastropaolo, D. et al., "Crystal and molecular structure of paclitaxel (taxol)", Proc. Natl. Acad. Sci. USA., vol. 92, pp. 6920–6924 (1995).

Miller, R.W. et al., "Antileukemic Alkaloids from *Taxus wallichiana* Zucc.", J. Org. Chem., vol. 46, pp. 1469–1474 (1981).

Mukerjee, A.K., "β–Lactams: Retrospect and Prospect", Tetrahedron, vol. 34, pp. 1731–1767 (1978).

Mukerjee, A.K., "Reactions of Natural and Synthetic β–Lactams", Synthesis, pp. 547–589 (1975).

Mukerjee, A.K. et al., "Synthesis of β–Lactams", Synthesis, pp. 327–346 (1973).

Nagai, H. et al., "Facile Enzymatic Prepration of Enantiomeric β–Lactams", Chem. Pharm. Bull, vol. 40, No. 8, pp. 2227–2229 (1992).

Nicolau, K.C. et al., "Chemistry and Biology of Taxol", Angew. Chem. Int. Ed. Engl., vol. 33, pp. 15–44 (1994).

Ojima, I. et al., "Efficient and Practical Asymmetric Synthesis of the Taxol C–13 Side Chain, N–Benzoyl–(2R, 3S)–3–phenylisoserine, and Its Analogues via Chiral 3–Hydroxy–4–aryl–β–lactams through Chiral Ester Enolate–Imine Cyclocondensation", J. Org. Chem., vol. 56, pp. 1681–1683 (1991).

Ojma, I. et al., N–acyl–3–hydroxy–β–lactams as Key Intermediates for Taxotere and Its Analogs, Bioorganic & Medicinal Chemsitry Letters, vol. 3, No. 11, pp. 2479–2482 (1993).

Ojima, I. et al., "New and Efficient Approaches to the Semisynthesis of Taxol and Its C–13 Side Chain Analogs by Means of β–Lactam Synthon Method", Tetrahedron, vol. 48, No. 34, pp. 6985–7012 (1992).

Ojima, I. et al., "New and Efficient Routes to Norstatine and Its Analogs with High Enantiometric Purity by β–Lactam Synthon Method", Tetrahedron Letters, vol. 33, No. 39, pp. 5737–5740 (1992).

Ojima, I. et al., "Synthesis and Biological Activity of 3'–alkyl–and 3'–alkenyl–3'–dephenyldocetaxels", Bioorganic & Medicinal Chemistry Letters, vol. 4, No. 21, pp. 2631–2634 (1994).

Ojima, I. et al., "Synthesis of Novel 3'–Trifluoromethyl Taxoids Through Effective Kinetic Resolution of Racemic 4–$CF_3$–β–Lactams With Baccatins", Chirality, vol. 9, pp. 487–494 (1997).

Okumura, S. et al., "Synthesis of Various Kinds of Estersw by Four Microbial Lipases", Biochimica et Biophysica Acta, vol. 575, pp. 156–165 (1979).

Palomo, C. et al., "Highly Stereo Synthesis of α–Hydroxy β–Amino acids through β–Lactams: Application to the Synthesis of the Taxol and Bestatin Side Chains and Related Systems", Tetrahedron Letters, vol. 31, No. 44, pp. 6429–6432 (1990).

Parida, S. et al., "Substrate Structure and Solvent Hydrophobicity Control Lipase Catalysis and Enantioselectivity in Organic Media", J. Am. Chem. Soc., vol. 113, pp. 2253–2259 (1991).

Parness, J. et al., "Structure–Activity Study of Cytotoxicity and Microtubule Assembly In Vitro by Taxol and Related Taxanes", Biochemical and Biophysical Research Communications, vol. 105, No. 3, pp. 1082–1089 (1982).

Riss, T.L. et al., "Comparison of MTT, XTT, and a novel tetrazolium compound MTS for in vitro proliferation and chemosensitivity assays" (1067), Molecular Biology of the Cells: Abstracts, vol. 3, p. 184a (1992).

Rowinsky, E.K. et al., "The Clinical Pharmacology and Use of Antimicrotubule Agents in Cancer Chemotherapeutics", Pharmac. Ther., vol. 52, pp. 35–84 (1991).

Samaranayake, G. et al., "Modified Taxols. 5. Reaction of Taxol with Electrophilic Reagents and Preparation of a Rearranged Taxol Derivative with Tubulin Assembly Activity", J. Org. Chem., vol. 56, pp. 5114–5119 (1991).

Schulz, M. et al., "Synthesis of new N–radicals of tetrazan–1–yl", Chemical Abstracts, vol. 108, No. 37298c, p. 581 (1988).

Sénilh, V. et al., "Hémisynthèse de noveaux analogues du taxol. Étude de leur interaction avec la tubuline", C.R. Acad. Sc. Paris, t. 299, Série II, No. 5, pp. 1039–1043 (1984).

Sénilh, V. et al., "Mise en Évidence de Noveaux Analogues du Taxol Extraits de Taxus Baccata", Journal of Natural Products, vol. 47, No. 1, pp. 131–137 (1984).

Shimako, K. et al., "Optically active threo–3–phenylserine derivatives", Chemical Abstracts, vol. 105, No. 23102k, p. 537 (1986).

Smeets, J.W.H. et al., "Enzymatic enantioselective ester hydrolysis by carboxylesterase NP", Recl. Trav. Chim. Pays–Bas, vol. 111, pp. 490–495 (1992).

Solomons, T.W.G., Organic Chemistry, Third Edition, John Wiley & Sons, Inc., publ., pp. 992–997 (1984).

Sonnet, P.E. et al., "Methyl–Branched Octanoic Acids as Substrates for Lipase–Catalyzed Reactions", Lipids, vol. 26, pp. 295–300 (1991).

Spencer, C.M. et al., "Paclitaxel: A Review of its Pharmacodynamic and Pharmacokinetic Properties and Therapeutic Potential in the Treatment of Cancer", Drugs, vol. 48, No. 5, pp. 794–847 (1994).

Steglich, W. et al., "1,3–oxazin–6–ones: Versatile Intermediates in Heterocyclic Synthesis", Gazzetta Chimica Italiana, vol. 116, pp. 361–372 (1986).

Stenesh, J., Dictionary of Biochemistry, John Wiley & Sons, Inc., publ., p. 101 (1975).

Stout, G.H. et al., Chapter 3: "Symmetry Operations and Space Groups", X–ray Structure Determination: A Practical Guide, The Macmillan Company, publ., pp. 38–61 (1968).

"Taxol® (paclitaxel) for Injection Concentrate", Physicians' Desk Reference, 49th Edition, Medical Economics Data Production Company, publ., pp. 682–685 (1995).

Tomiuchi, Y. et al., "Enzymatic Reactions in Aqueous–Organic Media. XVII. Optical Resolution of Amino Acid Esters by Enzymatic Hydrolysis in Organic Solvents", Bull. Chem. Soc. Jpn., vol. 65, pp. 2599–2603 (1992).

Wani, M.C. et al., "Plant Antitumor Agents. VI. The Isolation and Structure of Taxol, a Novel Antileukemic and Antitumor Agent from Taxus brevifolia", Journal of the American Chemical Society, vol. 93, No. 9, pp. 2325–2327 (1971).

Wells, J.N. et al., "The Synthesis of 2–Azetidinones", The Journal of Organic Chemistry, vol. 34, No. 5, pp. 1477–1479 (1969).

Witherup, K.M. et al., "High Performance Liquid Chromatographic Separation of Taxol and Related Compounds from Taxus Brevifolia," Journal Chromatography, vol. 12, No. 11, pp. 2117–2132 (1989).

Witherup, K.M. et al., "Taxus spp. Needles Contain of Taxol Comparable to the Bark of Taxus Brevifolia: Analysis and Isolation", Journal of Natural Products, vol. 53, No. 5, pp. 1249–1255 (1990).

Yamazaki, T. et al., "Preparation and Evaluation of Optically Active 4,4–Difluorothreonine as a Potent Novel Antitumor Material", Bioorganic and Medicinal Chemistry Letters, vol. 1, No. 5, pp. 271–276 (1991).

Yeh, M.–K. et al., "Some Taxane Derivatives from the Hearthwood of Taxus Mairel", Journal of the Chinese Chemical Society, vol. 35, pp. 309–313 (1988).

Zakhs, V.E. et al., "Oxo Derivatives of 1,3–oxazines (Review)", Chemistry of Heterocyclic Compounds; vol. 11, pp. 1149–1168 (1988).

Zhang, Z. et al., "Taxanes from Taxus Yunnanensis", Phytochemistry, vol. 29, No. 11, pp. 3673–3675 (1990).

Kingston, D.G.I. et al., "The Taxane Diterpenoids", Progress in the Chemistry of Organic Natural Products, vol. 61, Springer–Verlag, Wien, N.Y., publ., Herz, W. et al., eds., pp. 145–150 (1993).

* cited by examiner

PACLITAXEL SOLVATES

This application claims priority of U.S. Provisional Application No. 60/334,896, filed Nov. 30, 2001, the entire disclosure of which is incorporated herein by reference.

TECHNICAL BACKGROUND AND FIELD OF INDUSTRIAL APPLICABILITY

1. Field of the Invention

The invention is directed to novel crystalline solvates of paclitaxel with organic solvents, which are useful as sources of paclitaxel for therapeutic treatments. The inventive concept further includes methods of forming such solvates from paclitaxel-containing materials, and methods of obtaining paclitaxel from these solvates.

2. Description of Related Art

Paclitaxel, a diterpene taxane compound with significant antineoplastic properties having the structure:

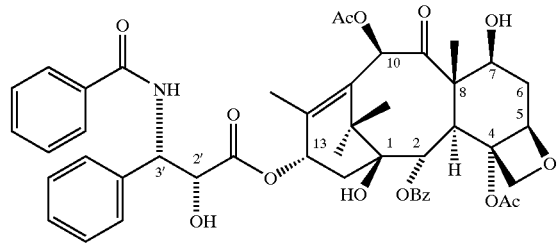

is a natural product first extracted from the bark of the Pacific yew tree, *Taxus brevifolia*. It is commercially available as Taxol®, Bristol-Myers Squibb Co. Taxol® has been shown to have excellent antitumor activity in in vivo animal models, and recent studies have elucidated its unique mode of action, which involves abnormal polymerization of tubulin and disruption of mitosis during the cell cycle. Taxol® has been approved for the treatment of refractory advanced ovarian cancer, breast cancer, non-small cell lung cancer and AIDS-related Kaposi's Sarcoma.

The results of paclitaxel clinical studies are reported in scientific periodicals and have been reviewed by numerous authors, such as Rowinsky et al., *Pharmac. Ther.*, 52, 35–84 (1991); Spencer et al., Drugs, 48 (5), 794–847 (1994); K. C. Nicolau et al., *Angew. Chem., Int. Ed. Eng.*, 33, 15–44 (1994); F. A. Holmes et al., "Taxane Anticancer Agents— Basic Science and Current Status", edited by Gunda I. Georg et al., 31–57 American Chemical Society, Washington, D.C. (1995); S. G. Arbuck et al., "Taxol® Science and Applications", edited by Matthew Suffness, 379–416, CRC Press, Boca Raton, Fla. (1995), and the references cited therein.

The patent literature describes many methods of isolating paclitaxel from plant sources, many of which involve extraction with various organic solvent systems followed by chromatographic separation.

The procedures described in U.S. Pat. Nos. 5,380,916, 5,475,120, and 5,670,673 to Rao (also PCT Publication No. WO 92/07842), for example, use a series of solvent extractions employing ethanol, chloroform, ligroin, benzene and methanol followed by reverse phase chromatography using a HPLC column with an acetonitrile eluent.

The procedures described in U.S. Pat. Nos. 5,279,949 and 5,478,736 to Nair (also PCT Publication No. WO 97/09443) use activated charcoal for decolorizing an initial 70% ethanol/water extract and early filtration through Celite® (diatomaceous earth). The decolorized extract is subsequently extracted with ethyl acetate, and evaporated to precipitate taxanes. The taxanes are re-dissolved in ethyl acetate and loaded onto a first silica column that is eluted with a hexane/ethyl acetate gradient, and further purified by tandem silica columns or, alternatively, by reverse phase chromatography.

U.S. Pat. No. 6,136,989 discloses a method of making an acetone mixture containing paclitaxel which includes extracting a paclitaxel-containing material with methanol to obtain a methanol extract; partitioning the methanol extract by liquid-liquid extraction with methylene chloride and water to form a two phase system having a methanolic phase containing methanol/water and a methylene chloride phase containing methylene chloride and paclitaxel; removing methanol and water from the methylene chloride phase to obtain a concentrated extract containing paclitaxel; contacting the concentrated extract with a silica matrix then eluting the silica matrix to obtain an eluate containing at least 5% (w/w) paclitaxel and adding acetone to the eluate to obtain an acetone mixture. According to the patent, acetone/water precipitation of an acetone mixture containing at least 5% paclitaxel will provide a precipitate containing at least 20% paclitaxel, and an acetone/water precipitation of an acetone mixture containing at least 10% paclitaxel will provide a precipitate containing 40% to 50% paclitaxel.

While the above patents are directed to the isolation of paclitaxel, none of them describes the crystallization of a novel, previously unknown paclitaxel solvate from a solution of paclitaxel and one or more organic solvents.

Paclitaxel has been used with organic solvents in the prior art in the development of pharmaceutical formulations. Paclitaxel is known to be poorly soluble in water, which limits the available formulations for administering paclitaxel to a patient. The formulation usually used contains 50% (v/v) alcohol and an 88-fold excess of polyoxyethylated castor oil (Cremophor® EL).

Various efforts have been made to discover other media for administration of paclitaxel to a patient. For example, U.S. Pat. No. 5,877,205 describes paclitaxel dissolved in a first organic solvent (e.g. N,N'-dimethylacetamide or dimethylsulfoxide), followed by a secondary solvent, such as polyethyleneglycol 400, for final dilution in an aqueous solvent.

U.S. Pat. No. 6,017,948 discloses paclitaxel formulations asserted to be suitable for administration to a patient comprising a solution of paclitaxel in water-miscible, non-aqueous solvents, such as N-methyl pyrrolidone, propylene glycol, ethyl acetate, dimethyl sulfoxide, N,N'-dimethylacetamide, benzyl alcohol, 2-pyrrolidone, or benzyl benzoate.

Both the above-mentioned patents are directed to liquid formulations for administration by infusion. None of the above patents discloses the crystallization of paclitaxel solvates from their respective formulations.

SUMMARY OF THE INVENTION

Distinct crystalline forms of paclitaxel are known to exist. The present invention is directed, in one aspect, to novel biologically active organic solvates of paclitaxel which exist in crystalline form and from which high purity paclitaxel can be isolated.

The novel solvates of paclitaxel described herein are previously unknown, three-dimensionally crystalline arrangements of paclitaxel molecules, which include sites for suitable organic solvent molecules. Suitable organic solvents are those having molecules which can be incorporated in the solvent sites without changing the unique arrangement of the paclitaxel molecules as described herein.

Such novel solvates of paclitaxel have been found to be useful intermediates in the purification of paclitaxel. The solvates themselves have been found to have biological activity.

In certain embodiments, the novel solvates described herein may be obtained from a paclitaxel-containing material such as a crude taxane mixture wherein the taxanes are derived, for example, from natural sources. In other embodiments, the novel solvates may be obtained from semi-synthetic paclitaxel, or from mixtures prepared from relatively pure paclitaxel dissolved in one or more organic solvents.

In another aspect, the invention comprises a method for the preparation of crystalline paclitaxel solvates from a mixture comprising a paclitaxel-containing material, and an organic solvent having solvent molecules compatible with solvent sites in the unique crystalline arrangement of paclitaxel molecules as hereinbefore described. The solid, crystalline paclitaxel solvate containing paclitaxel and solvent molecules within the crystal structure is isolated from the mixture.

The invention further comprises a method of recovering paclitaxel from the solvates described herein, comprising removing solvent molecules from the crystalline solvate structure. This process is referred to herein as a "desolvation" step, and may be accomplished using any solvent removal means known in the art.

Yet another aspect of the instant invention concerns methods for inhibiting human and/or other mammalian tumors which comprises administering to a tumor-bearing host an anti-tumor effective amount of these novel paclitaxel forms.

DETAILED DESCRIPTION OF THE PREFERRED EMBODIMENTS

Figure 1:
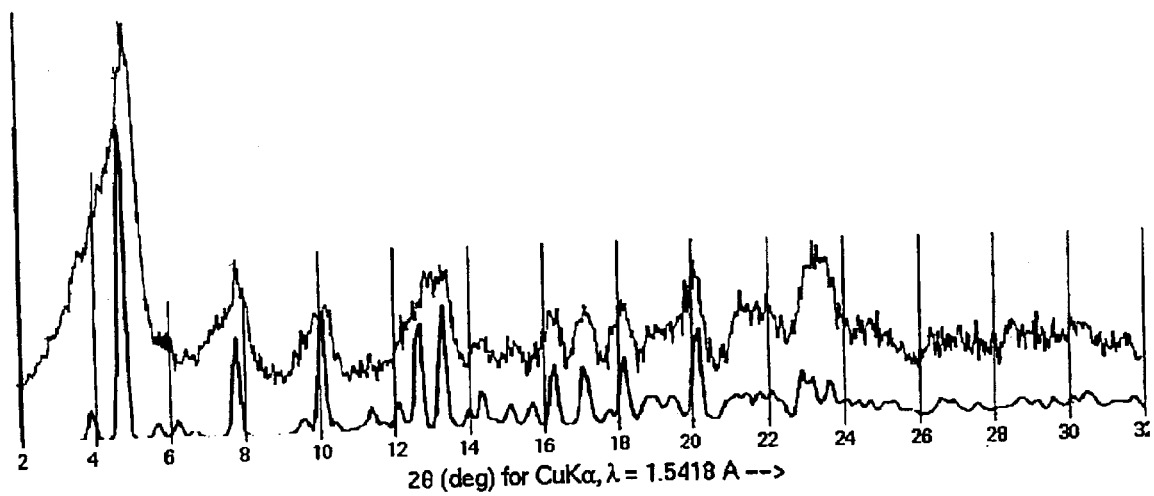
FIG. 1 is an observed powder X-ray diffraction (PXRD) pattern of bulk Form D, a previously unknown crystalline paclitaxel solvate in which NMPO, acetonitrile and water are incorporated in the crystal structure. The observed upper pattern (measured from a slurry in the original solvent mixture at RT) agrees well with the lower pattern simulated from atomic coordinates obtained from complete X-ray analysis of a single crystal at −43° C.
Figure 2:
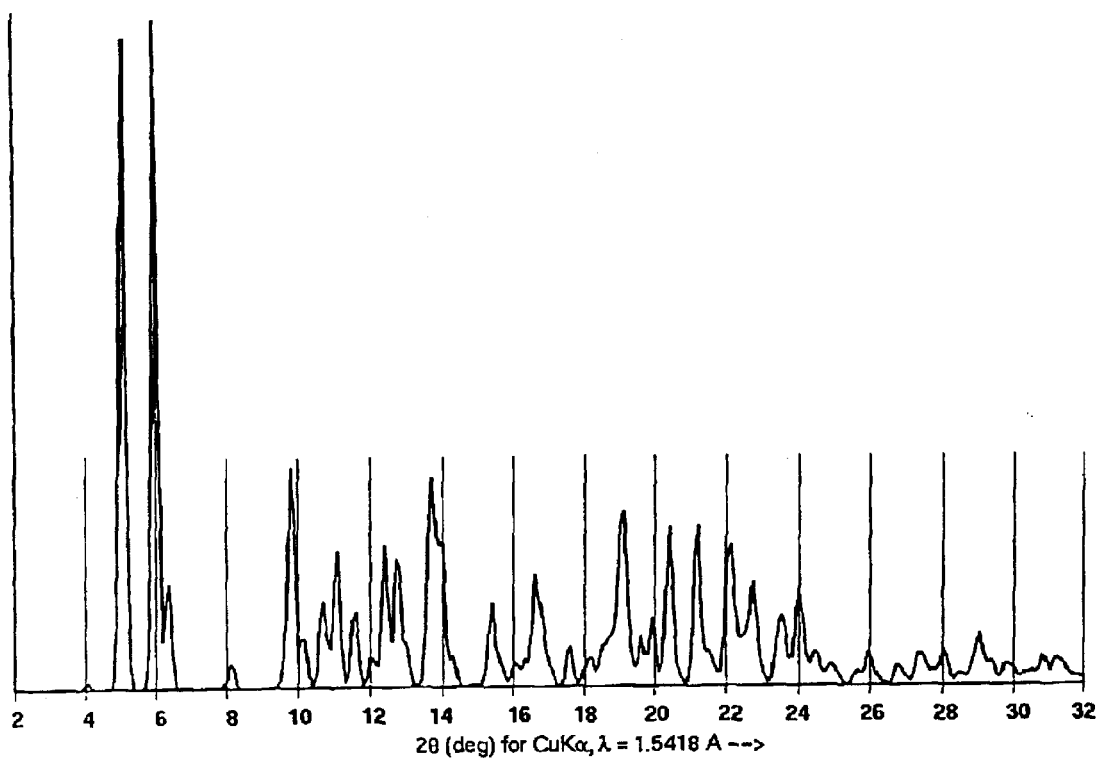
FIG. 2 is a simulated powder X-ray diffraction (PXRD) pattern of Form E, a previously unknown crystalline paclitaxel solvate in which DMF and water are incorporated in the crystal structure. This simulated pattern was calculated from atomic coordinates obtained from complete single X-ray analysis at −53° C.

Paclitaxel for use in commercial Taxol® is manufactured as a solvent-free crystalline powder (referred to herein as Form A). In the process of characterizing the present invention, it has been determined through single crystal X-ray diffraction studies that Form A is orthorhombic, and its unit cell contains two crystallographically independent molecules of paclitaxel associated with hydrogen bonds to form a hydrogen-bonded "dimer," and no solvent molecules. As used herein, the phrase "paclitaxel dimer" and the term "dimer" refer to two paclitaxel molecules that are hydrogen-bonded to each other. A network of eleven hydrogen bonds joins the two paclitaxel molecules to symmetry-related neighbors. Another feature of this arrangement is the presence of a large solvent site buried in a cleft between the two independent paclitaxel molecules; however, the crystal structure, and therefore the arrangement of paclitaxel molecules in form A is entirely different from any of the novel forms disclosed herein.

Paclitaxel Form A (elongated thin plates) exists primarily as a highly water insoluble crystalline, granular, solvent-free form. It is substantially non-hygroscopic under normal laboratory conditions (relative humidity (RH) approximately 50–60%; 20–30° C.). However, when contacted with an atmosphere having a relative humidity greater than about 90%, or in aqueous suspensions, dispersions or emulsions, Form A converts (as a function of time, temperature, agitation, etc.) to a thermodynamically more stable form (referred to herein as Form B). Form B is a trihydrate orthorhombic form having six water sites per two independent paclitaxel molecules (one paclitaxel "dimer"). These hydrated crystals are of a fine, hair-like appearance and are even less water soluble than Form A.

The Form B trihydrate is formed in aqueous suspensions or through crystallization from aqueous solvents in the presence of a large excess of water. This form is disclosed in the commonly assigned patent application EP 717,041, which is herein incorporated by reference in its entirety. In the process of characterizing the present invention, it has been determined through single crystal X-ray diffraction studies that Form B is orthorhombic, and its unit cell contains two crystallographically independent molecules of paclitaxel associated with hydrogen bonds to form a "dimer". The crystal structure, and therefore the arrangement of paclitaxel molecules in form B is entirely different from form A and any of the novel forms disclosed herein.

Mastropaolo, et al. disclosed a novel crystalline solvate of paclitaxel obtained by evaporation of solvent from a solution of Taxol® in dioxane, water and xylene. Proc. Natl. Acad. Sci. USA 92, 6920–24 (July, 1995). This solvate is referred to herein as Form C, however it is indicated as being unstable, and, in any event, has not been shown to effect purification of crude paclitaxel, unlike the novel solvates of the present invention. The thin plate-like crystals are reported to contain five water molecules and three dioxane molecules per two molecules of paclitaxel. The crystal structure, and therefore the molecular arrangement of paclitaxel molecules in form C is entirely different from any of the novel forms disclosed herein.

According to an embodiment of the present invention, novel, relatively stable, paclitaxel solvates are crystallized in a controlled fashion from a solution comprising paclitaxel-containing material in one or more organic solvents. The crystallization is effected by adding water as an anti-solvent in a controlled manner, in conjunction with temperature oscillation. In this respect, the water is added in aliquots such that the crystallization of the novel solvate is favored over the precipitation of the trihydrate. This control optimizes yield and quality of the crystalline paclitaxel solvate and substantially avoids formation of the trihydrate.

Preferably, the organic solvents are selected from the group consisting of dimethylsulfoxide (DMSO), N,N'-dimethylformamide (DMF), N,N'-dimethylacetamide (DMAC), N-methyl-2-pyrrolidone (NMPO), 1,3-dimethyl-2-imidazolidinone (DMEU), 1,3-dimethyl-3,4,5,6-tetrahydro-2-(1H)-pyrimidinone (DMPU), and acetonitrile and mixtures thereof. However, other solvents compatible with the solvent sites in the crystalline structures of the presently disclosed solvates may also be used. Various examples of solvates that are formed with one or more of these solvents are described below.

For example, in one embodiment of form E, crystallization from a solution comprising paclitaxel and aqueous DMF yields a solvate having the apparent molecular ratio of DMF:paclitaxel of about 0.5:1. In a preferred embodiment of form E, crystallization from a solution of paclitaxel in aqueous DMF yields a ternary crystal structure, which contains one DMF solvent molecule and about two water molecules per paclitaxel "dimer".

In one embodiment of form D, crystallization from a solution comprising paclitaxel and aqueous NMPO yields a solvate having the apparent molecular ratio of NMPO:paclitaxel of about 1:1. In a preferred embodiment of form D, crystallization from an aqueous solution comprising paclitaxel, acetonitrile ($CH_3CN$), acetic acid, and NMPO yields a Form D solvate characterized by about three molecules of water, about two molecules of NMPO, and about one molecule of acetonitrile per two molecules of paclitaxel ("dimer").

In another embodiment, precipitation from a solution comprising paclitaxel and aqueous DMPU yields a solid of unknown structure containing DMPU and paclitaxel in the approximate molecular ratio of 1:1.

In another embodiment, precipitation from a solution comprising paclitaxel and aqueous DMSO yields a solid of unknown structure containing DMSO and paclitaxel in the approximate molecular ratio of 1–2:1.

The solvates of this invention should be interpreted as including equivalents having similar crystal structures, properties and approximately the same ratio of solvents to paclitaxel.

The process of preparing the solvates includes combining a paclitaxel-containing material, which may be derived from various sources, with an aqueous solution of one or more organic solvents. The mixture may optionally include an acidifying agent to suppress the formation of an isomer, 7-epi-paclitaxel. Any suitable acidifying agent may be used. Non-limiting examples of these include dilute acetic or citric acids. The solids formed by combining the paclitaxel with the solvents may then be isolated by filtration, and excess, non-crystalline solvent removed by any means known in the art. The resulting isolated product contains a proportion of solvent within the crystalline solvate form. The isolated solvate may, in a subsequent step, be "desolvated," i.e. exposed to solvent removal means known in the art to remove the solvent molecules from the crystalline structure and effect the conversion of the solvate, for example, to paclitaxel form A. The form E solvate of the present invention may also optionally be converted to form B by desolvation.

The solvates described herein, and particularly the Form D NMPO solvate of paclitaxel, unexpectedly improves the purity of paclitaxel derived from crude product streams. When dissolved, the solvates also have biological activity similar to Form A. Furthermore, they may be converted to Form A by heating under vacuum. Form D transforms to form A, even under conditions of relatively high humidity.

In one embodiment, the invention comprises a method for isolating paclitaxel solvates comprising contacting a paclitaxel-containing material, such as a crude mixture of taxanes obtained from plant sources, with an organic solvent, optionally with heating to promote dissolution of the paclitaxel. The crude mixture of taxanes is generally a mixture of taxanes in an organic solvent obtained by extracting the plant sources with solvent. An acidifying agent is preferably added. The solvate may then be precipitated from the mixture as described herein. After precipitation, the slurry is filtered to isolate the solvate.

The quality of slurry that can be produced from a given amount of crude taxane mixture and organic solvent is increased if the temperature is first raised to a temperature at which the slurry thins, then lowered until the slurry thickens, and then repeating this procedure for a plurality of cycles. The upper and lower temperature set points can be adjusted and optimized for a given solvent system by one of ordinary skill in the art without undue experimentation.

The isolation procedure is also effective for purifying material containing crude and semi-synthetic paclitaxel and presumably, may also be effective using completely synthetic paclitaxel.

In the detailed description that follows, all specified quantities and process conditions (including time, temperature, and the like) are exemplary only and are understood to include a range of equivalents. All such numerical examples are understood to be modified by the term "about," whether or not this is explicitly stated, and the scope of the term "about" is a range of values as could be determined by one of ordinary skill in the art without undue experimentation.

Suitable paclitaxel-containing material for paclitaxel isolation may be selected from any tissue that contains a high paclitaxel content, preferably at least about 0.005 percent by weight on a dry basis. Examples of suitable paclitaxel-containing material include tissues from various species of Yew plants comprising the genus Taxus, most preferably the bark of *T. brevifolia,* or *T. yunnanensis,* and the roots and needles of ornamental Yew plants such as *T. cuspidata, T. x media* spp *Hicksii, T. x dark green spreader* and Hill., *T. chinensis, T. wallichiana, T. canadensis, T. globosa, T. sumatrana,* and *T. floridana.* Other suitable materials include cultures of plant tissues obtained from a Taxus species. Methods for obtaining cultured tissue are generally described, for example, in U.S. Pat. No. 5,744,333, European Patent No. 553,780 B1 to Cociancich and Pace and U.S. Pat. No. 5,451,392 to Strobel et al.

The paclitaxel-containing material may also be obtained from semi-synthetic or otherwise natural sources. U.S. Pat. No. 5,451,392, for example, describes media for culturing cells which is also suitable for the practice of this invention. Also, microorganisms expressing extractable paclitaxel are suitable, e.g., in cell paste or fermentation broth. Examples of suitable microorganisms are species of Erwinia associated with some Taxus species as described in U.S. Pat. No.

5,451,392 to Page et al. Another example includes microorganisms of the genus Taxomyces, and more specifically, *Taxomyces andreanae*, which are capable of producing paclitaxel. Still other examples include microorganisms engineered to produce paclitaxel using recombinant DNA techniques.

In other embodiments, the solvates are obtained by precipitation from an aqueous solution comprising relatively pure paclitaxel and an organic solvent or mixture of organic solvents. While not limiting the invention, relatively pure paclitaxel used in this manner generally has a purity greater than about 90%.

In precipitating the solvates, seeding may optionally be used to initiate crystallization. In this respect, seed crystals of the desired solvate may be introduced to the solution to induce solvate formation.

The present invention further provides a method for the conversion of the novel crystalline paclitaxel solvates into Form A paclitaxel, which is used in commerce. Preferably, the conversion comprises drying the solvate under vacuum at an elevated temperature. In a preferred embodiment, a crystalline paclitaxel solvate of the present invention is desolvated and converted into Form A paclitaxel during drying in vacuo, at a suitable combination of vacuum and temperature.

The compounds of the invention exhibit anti-tumor activity both in vitro and in vivo. For treating a variety of tumors, the compounds of the invention may be used in a manner similar to that of paclitaxel Form A; e.g., see Physician's Desk Reference, 49th Edition, Medical Economics, p. 682, 1995. The dosage, mode, and schedule of administration for the compounds of the invention are not particularly restricted. An oncologist skilled in the art of cancer treatment will be able to ascertain, without undue experimentation, an appropriate treatment protocol for administering the compound of the present invention. Thus, the active compounds may be administered via any suitable route of administration, parenterally or orally. Parenteral administration includes intravenous, intraperitoneal, intramuscular, and subcutaneous administration.

The doses utilized to implement the treatment methods of the invention are the ones that make it possible to administer prophylactic treatment or to evoke a maximal therapeutic response. The doses vary, depending on the type of administration, the particular product selected, and the personal characteristics of the subject to be treated. In general, the doses are the ones that are therapeutically effective for the treatment of disorders caused by abnormal cell proliferation. The compounds of the invention can be administered as often as necessary in order to obtain the desired therapeutic effect. Some patients may respond rapidly to relatively high or low doses, and then require mild maintenance or no maintenance dose at all. Via the i.v. route, the dosage may be, for example, in the range of about 20 to about 500 mg/m2 over 1 to 100 hours. Via the oral route, the dosage may be in the range of 5–1000 mg/kg body weight/day. The actual dose used will vary according to the particular composition formulated, the route of administration, and the particular site, host, and type of tumor being treated. Many factors that modify the action of the drug will be taken into account in determining the dosage including age, weight, sex, diet and the physical condition of the patient.

The present invention also provides pharmaceutical compositions containing an anti-tumor effective amount of active compound in combination with one or more pharmaceutically acceptable carriers, excipients, diluents, or adjuvants. The compositions can be prepared in accordance with conventional methods. The examples in U.S. Pat. Nos. 4,960,790 and 4,814,470 may be followed to formulate the compositions of this invention. For example, active compounds may be formulated as tablets, pills, powder mixtures, capsules, injectables, solutions, suppositories, emulsions, dispersions, food premix, and in other suitable forms. They may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical pharmaceutically acceptable carriers are, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, and silicic acid.

The pharmaceutical preparation may also contain non-toxic auxiliary substances such as emulsifying, preserving or wetting agents, and the like, such as sorbitan monolaurate, triethanolamine oleate, polyoxyethylene monostearate, glyceryl tripalmitate, and dioctyl sodium sulfosuccinate, and the like.

The following examples describe the manner and process of making and using the invention and are intended to be illustrative rather than limiting.

EXAMPLE 1

Paclitaxel Solvate Form D (NMPO)

533 mg of paclitaxel was dissolved in 26.6 mL of NMPO. To this was added 13.3 mL of acetonitrile, and then 13.3 mL of 0.1% aqueous acetic acid. The solution was heated to 40° C., and a 0.1% aqueous acetic acid solution (26.6 mL) was added in two portions. This was then cooled to 20° C. over 90 minutes and sonicated. The slurry was then heated to 58° C. and then cooled to 20° C. over 90 minutes. The slurry was then heated to 58° C., stirred for 1 hour and cooled to 20° C. over 4.5 hours. The slurry was then sonicated, reheated to 58° C. over 30 minutes and stirred at 58° C. for 1 hour. The slurry was then cooled to 20° C. over 4.5 hours, and stirred slowly for 16 hours. The slurry was then decanted and filtered. The filter cake was washed with 25% acetonitrile in 0.1% aqueous acetic acid (2 mL). The filter cake was then dried under high vacuum at 40° C. to yield a colorless solid (450 mg). The ratio of NMPO to paclitaxel by 1H NMR was 1.0:1, consistent with the single crystal structure of form D (potency=855 µg/mg; area % was 99.7). (Form D crystals ideally contain $H_2O$, NMPO, $CH_3CN$, and paclitaxel in the molar ratio 3:2:1:2).

The Form D NMPO solvate crystals consisted of thin elongated plates having the following unit cell parameters at −43° C. (A detailed account of unit cells can be found in Chapter 3 of Stout & Jensen, X-Ray Structure Determination: A Practical Guide, MacMillan Co., New York (1968), herein incorporated by reference.)

Cell dimensions:
 a=9.541(1) Å
 b=28.456(4) Å
 c=37.238(5) Å

Volume: 10,110 Å³

Space Group: P 2₁ 2₁ 2₁ orthorhombic

Ideal composition of the unit cell: 8 paclitaxel, 8 NMPO, 4 CH$_3$CN, 12 H$_2$O

Density (calculated): 1.315 g/cm³

Figure 3:
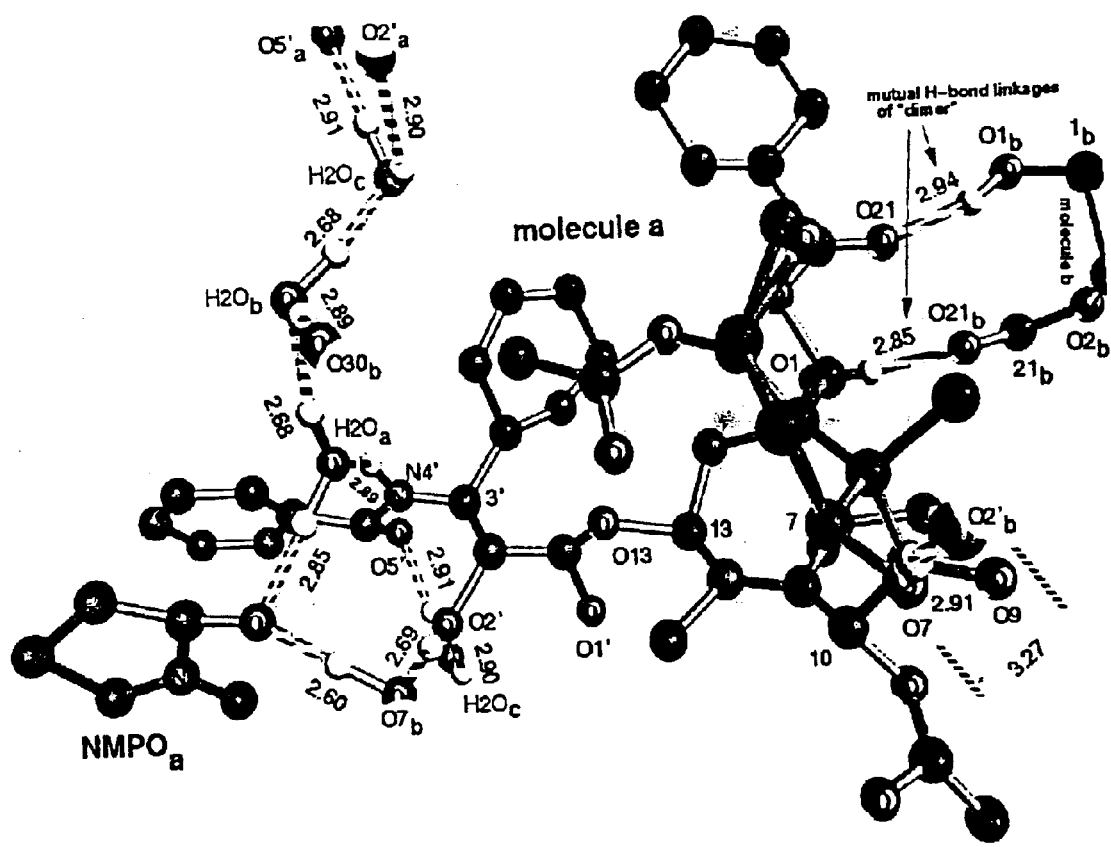
FIG. 3 is a depiction of the solid state arrangement of a paclitaxel molecule and solvent molecules in one part of the Form D solvate, based on the observed atomic coordinates. The acetonitrile molecule is not shown.
Figure 4:
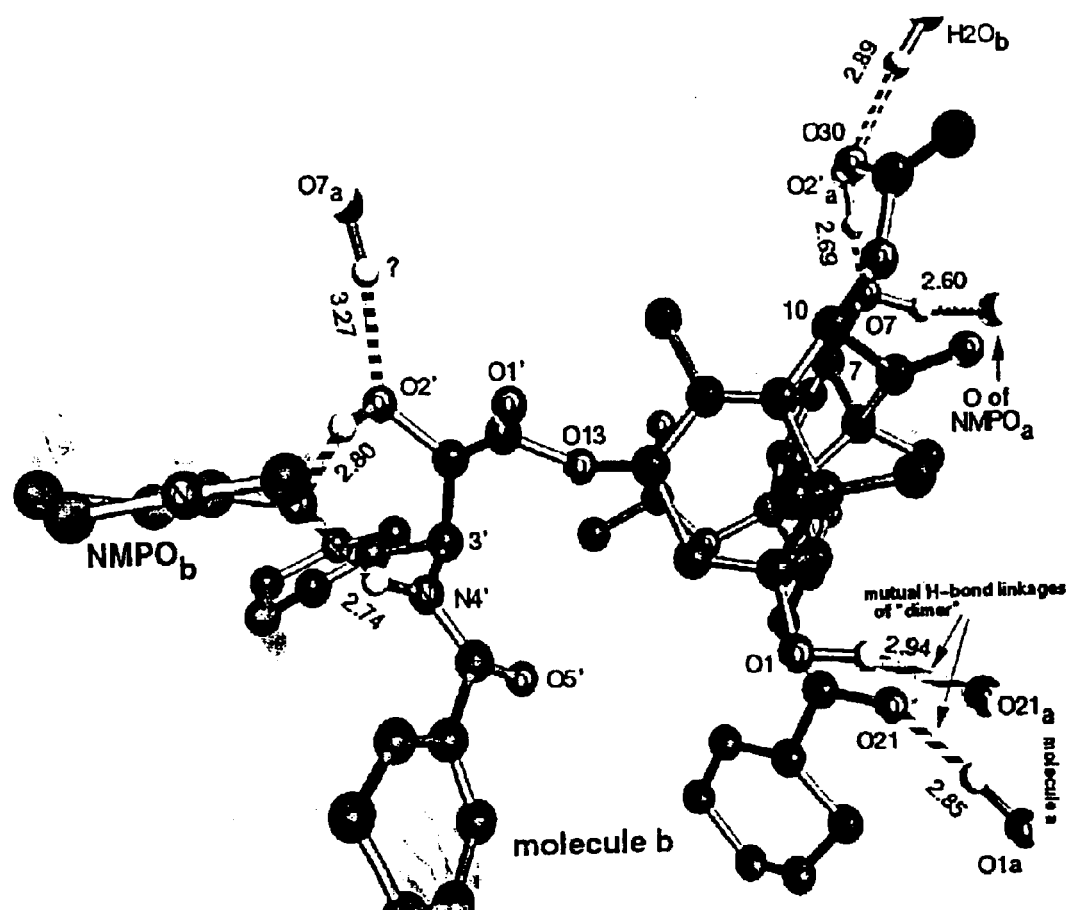
FIG. 4 is a depiction of the solid state arrangement of symmetry-independent paclitaxel and solvent molecules in another part of the Form D solvate, based on the observed atomic coordinates. The acetonitrile molecule is not shown.

The unique arrangements of paclitaxel and solvent molecules in form D are illustrated in FIGS. 3 and 4, and are based on the fractional atomic coordinates listed in Tables 1–2 below.

The approximate fractional coordinates reported for each form in Tables 1–3 encompass additional isomorphic crystalline solvate forms composed of paclitaxel and solvents other than the solvents exemplified. In the Tables, atom numbers less than 40 represent atoms in molecule "b" of the paclitaxel "dimer". The corresponding atoms in molecule "a" have numbers forty greater than corresponding atoms in molecule "b". Thus, for example, "N44'" in Table 1 is in molecule "a", and corresponds to N4' of molecule "b". Molecule "a" and molecule "b" are the two molecules of the paclitaxel "dimer", labeled in the Figures. Atoms O111, O112, and O113 are the three water molecules. Atoms N101, C102, and C103 are the acetonitrile molecules. Atoms N91, O92, and C93–C96 are one of the two NMPO solvent molecules. Except for some slight natural lattice expansion, the crystal structure remains the same under ambient conditions. The approximate coordinates in Table 1 therefore will vary according to the temperature at measurement. Statistical variations in these coordinates may also occur consistent with the reported error values.

TABLE 1

| Atom | X | Y | Z | B(A2) |
|---|---|---|---|---|
| C44 | 0.219 (3) | 0.0264 (9) | 0.2022 (7) | 1.2 (7) |
| C41 | 0.517 (3) | 0.092 (1) | 0.1537 (7) | 1.6 (7) |
| C48 | 0.384 (3) | 0.072 (1) | 0.2427 (7) | 1.9 (7) |
| C55 | 0.653 (4) | 0.108 (1) | 0.1774 (8) | 2.3 (8) |
| C51 | 0.681 (4) | 0.063 (1) | 0.2022 (9) | 3.4 (9) |
| C62 | 0.098 (4) | 0.099 (1) | 0.1032 (9) | 3.6 (9) |
| C52' | 0.573 (3) | -0.076 (1) | 0.0594 (7) | 1.7 (7) |
| C49 | 0.526 (4) | 0.098 (1) | 0.2529 (8) | 2.1 (8) |
| C61 | 0.198 (4) | 0.115 (1) | 0.1297 (8) | 2.4 (8) |
| C41' | 0.758 (4) | -0.058 (1) | 0.1229 (8) | 2.7 (8) |
| C45' | 0.768 (5) | -0.172 (1) | 0.038 (1) | 7.9 (14) |
| C52 | 0.701 (3) | 0.0231 (9) | 0.1857 (7) | 1.1 (7) |
| C68 | 0.295 (4) | -0.050 (1) | 0.1792 (8) | 2.1 (8) |
| C70 | 0.840 (4) | 0.088 (1) | 0.287 (1) | 5.6 (11) |
| C43 | 0.368 (3) | 0.0519 (9) | 0.2045 (7) | 0.5 (6) |
| C50 | 0.665 (3) | 0.071 (1) | 0.2403 (8) | 2.1 (8) |
| C42 | 0.368 (3) | 0.0920 (9) | 0.1747 (7) | 0.4 (6) |
| C43' | 0.689 (3) | -0.1076 (9) | 0.0705 (7) | 0.9 (7) |
| C53 | 0.687 (3) | 0.019 (1) | 0.1454 (8) | 2.4 (8) |
| C45 | 0.157 (3) | 0.005 (1) | 0.2369 (8) | 2.4 (8) |
| C42' | 0.712 (4) | -0.108 (1) | 0.1154 (8) | 2.5 (8) |
| C47 | 0.376 (3) | 0.031 (1) | 0.2696 (8) | 2.1 (7) |
| C63 | 0.087 (4) | 0.049 (1) | 0.0956 (9) | 4.9 (10) |
| C67 | 0.033 (3) | 0.136 (1) | 0.0854 (7) | 1.6 (7) |
| C57' | 0.441 (4) | -0.090 (1) | 0.0602 (9) | 4.8 (10) |
| C53' | 0.613 (4) | -0.031 (1) | 0.046 (1) | 5.8 (11) |
| C64 | -0.020 (4) | 0.036 (1) | 0.0694 (9) | 4.9 (11) |
| C66 | -0.074 (4) | 0.122 (1) | 0.0603 (8) | 3.4 (9) |
| C54' | 0.498 (4) | 0.001 (1) | 0.0377 (8) | 2.6 (8) |
| C56' | 0.334 (4) | -0.061 (1) | 0.051 (1) | 5.1 (11) |
| C65 | -0.088 (4) | 0.074 (1) | 0.052 (1) | 5.0 (10) |
| C55' | 0.362 (4) | -0.014 (1) | 0.0372 (8) | 2.7 (8) |
| O44 | 0.235 (2) | -0.0071 (7) | 0.1735 (5) | 2.3 (5) |
| O50 | 0.779 (2) | 0.0972 (7) | 0.2539 (5) | 3.3 (5) |
| O42 | 0.277 (2) | 0.0788 (6) | 0.1461 (4) | 1.0 (4) |
| O53 | 0.646 (2) | -0.0335 (6) | 0.1366 (5) | 1.8 (5) |
| O45 | 0.036 (2) | 0.0369 (7) | 0.2317 (5) | 3.4 (6) |
| O49 | 0.544 (2) | 0.1271 (8) | 0.2745 (5) | 3.5 (6) |
| O61 | 0.211 (2) | 0.1540 (6) | 0.1434 (5) | 1.0 (4) |
| O41' | 0.872 (3) | -0.0418 (7) | 0.1206 (6) | 3.9 (6) |

TABLE 1-continued

| Atom | X | Y | Z | B(A2) |
|---|---|---|---|---|
| O45' | 0.855 (3) | -0.156 (1) | 0.0227 (7) | 8.6 (9) |
| O68 | 0.359 (2) | -0.0540 (7) | 0.2077 (5) | 3.3 (6) |
| O70 | 0.802 (3) | 0.0504 (8) | 0.2991 (6) | 5.1 (7) |
| N44' | 0.669 (3) | -0.1571 (9) | 0.0608 (7) | 3.5 (7) |
| C54 | 0.553 (3) | 0.0428 (9) | 0.1321 (7) | 0.7 (7) |
| C46 | 0.229 (4) | 0.010 (1) | 0.2720 (8) | 2.5 (8) |
| C60 | 0.084 (4) | 0.053 (1) | 0.1934 (8) | 3.0 (9) |
| O41 | 0.494 (2) | 0.1261 (6) | 0.1247 (5) | 1.2 (4) |
| O42' | 0.824 (2) | -0.1385 (7) | 0.1229 (5) | 2.5 (5) |
| O47 | 0.415 (2) | 0.0416 (7) | 0.3046 (5) | 2.6 (5) |
| C59 | 0.275 (4) | 0.113 (1) | 0.2549 (8) | 3.1 (9) |
| C56 | 0.615 (3) | 0.1548 (9) | 0.1965 (7) | 0.8 (7) |
| C57 | 0.788 (3) | 0.117 (1) | 0.1527 (7) | 1.5 (7) |
| C58 | 0.734 (3) | -0.023 (1) | 0.2075 (8) | 2.5 (8) |
| C69 | 0.298 (3) | -0.083 (1) | 0.1483 (8) | 2.2 (8) |
| C71 | 0.950 (4) | 0.120 (1) | 0.2981 (8) | 3.0 (8) |
| C4 | 0.946 (3) | 0.161 (1) | -0.2152 (8) | 2.0 (8) |
| C1 | 0.631 (3) | 0.2169 (9) | -0.1612 (7) | 1.1 (7) |
| C8 | 0.780 (4) | 0.212 (1) | -0.2543 (8) | 2.7 (8) |
| C15 | 0.508 (3) | 0.238 (1) | -0.1862 (8) | 1.7 (7) |
| C11 | 0.474 (4) | 0.199 (1) | -0.2140 (9) | 3.9 (9) |
| C22 | 1.052 (3) | 0.225 (1) | -0.1124 (7) | 1.1 (7) |
| C6' | 0.473 (3) | 0.099 (1) | -0.0287 (8) | 2.1 (8) |
| C12' | 0.573 (3) | -0.032 (1) | -0.0938 (8) | 2.5 (8) |
| C9 | 0.642 (4) | 0.235 (1) | -0.2626 (8) | 2.7 (8) |
| C21 | 0.953 (4) | 0.240 (1) | -0.1397 (8) | 3.2 (9) |
| C1' | 0.386 (3) | 0.0635 (9) | -0.1493 (7) | 0.6 (6) |
| C5' | 0.545 (4) | 0.075 (1) | -0.0630 (9) | 4.7 (10) |
| C12 | 0.466 (3) | 0.1535 (9) | -0.2038 (7) | 1.0 |
| C28 | 0.850 (4) | 0.080 (1) | -0.1952 (8) | 3.2 (9) |
| C30 | 0.325 (4) | 0.236 (1) | -0.301 (1) | 4.8 (10) |
| C3 | 0.788 (3) | 0.1857 (9) | -0.2161 (7) | 0.6 (6) |
| C10 | 0.491 (3) | 0.207 (1) | -0.2537 (8) | 1.7 (7) |
| C2 | 0.770 (4) | 0.222 (1) | -0.1823 (8) | 2.5 (8) |
| C3' | 0.535 (4) | 0.019 (1) | -0.1081 (8) | 2.3 (8) |
| C13 | 0.466 (3) | 0.1421 (9) | -0.1625 (7) | 1.0 |
| C5 | 1.011 (3) | 0.139 (1) | -0.2506 (8) | 2.4 (8) |
| C2' | 0.444 (3) | 0.014 (1) | -0.1411 (8) | 2.1 (8) |
| C7 | 0.787 (3) | 0.171 (1) | -0.2825 (8) | 2.0 (8) |
| C23 | 1.082 (3) | 0.175 (1) | -0.1095 (7) | 1.3 (7) |
| C27 | 1.134 (3) | 0.258 (1) | -0.0928 (8) | 2.0 (7) |
| C11' | 0.572 (4) | 0.127 (1) | -0.0072 (9) | 5.0 (10) |
| C7' | 0.342 (4) | 0.091 (1) | -0.0169 (8) | 3.3 (9) |
| C17' | 0.525 (4) | -0.049 (1) | -0.0606 (9) | 4.2 (10) |
| C13' | 0.657 (5) | -0.059 (1) | -0.114 (1) | 6.8 (12) |
| C26 | 1.238 (4) | 0.245 (1) | -0.0687 (8) | 3.0 (8) |
| C24 | 1.192 (4) | 0.162 (1) | -0.0871 (9) | 3.9 (10) |
| C8' | 0.286 (4) | 0.110 (1) | 0.0165 (9) | 4.3 (10) |
| C10' | 0.530 (5) | 0.142 (1) | 0.027 (1) | 7.1 (12) |
| C16' | 0.564 (4) | -0.091 (1) | -0.0481 (9) | 5.1 (11) |
| C14' | 0.697 (4) | -0.104 (1) | -0.1009 (9) | 5.2 (11) |
| C25 | 1.264 (4) | 0.195 (1) | -0.0635 (9) | 3.8 (9) |
| C9' | 0.393 (4) | 0.137 (1) | 0.0367 (9) | 3.9 (9) |
| C15' | 0.650 (4) | -0.120 (1) | -0.0677 (9) | 5.1 (11) |
| O4 | 0.923 (2) | 0.1233 (7) | -0.1868 (5) | 1.9 (5) |
| O10 | 0.380 (2) | 0.2383 (7) | -0.2634 (5) | 3.0 (5) |
| O2 | 0.880 (2) | 0.2052 (6) | -0.1559 (5) | 1.5 (4) |
| O13 | 0.503 (2) | 0.0934 (7) | -0.1594 (5) | 2.7 (5) |
| O5 | 1.122 (2) | 0.1722 (7) | -0.2426 (5) | 2.7 (5) |
| O9 | 0.629 (2) | 0.2698 (6) | -0.2812 (5) | 1.4 (4) |
| O21 | 0.930 (2) | 0.2810 (7) | -0.1445 (5) | 2.2 (5) |
| O1' | 0.272 (2) | 0.0783 (7) | -0.1498 (5) | 3.2 (5) |
| O5' | 0.665 (3) | 0.0900 (8) | -0.0721 (6) | 4.1 (6) |
| O28 | 0.791 (2) | 0.0807 (7) | -0.2238 (5) | 3.2 (6) |
| O30 | 0.371 (3) | 0.2020 (9) | -0.3153 (6) | 5.9 (7) |
| N4' | 0.460 (3) | 0.0444 (8) | -0.0782 (6) | 1.5 (6) |
| C14 | 0.599 (3) | 0.165 (1) | -0.1470 (7) | 1.5 (7) |
| C6 | 0.947 (4) | 0.151 (1) | -0.2854 (8) | 2.9 (9) |
| C20 | 1.078 (3) | 0.188 (1) | -0.2072 (7) | 1.9 (8) |
| O1 | 0.648 (2) | 0.2464 (6) | -0.1304 (5) | 1.3 (4) |
| O2' | 0.324 (2) | -0.0158 (7) | -0.1374 (5) | 2.5 (5) |
| O7 | 0.742 (2) | 0.1856 (6) | -0.3173 (5) | 1.9 (5) |
| C19 | 0.891 (3) | 0.253 (1) | -0.2590 (7) | 1.6 (7) |
| C16 | 0.543 (3) | 0.287 (1) | -0.2021 (7) | 1.3 (7) |
| C17 | 0.369 (3) | 0.243 (1) | -0.1634 (7) | 1.4 (7) |
| C18 | 0.433 (3) | 0.113 (1) | -0.2291 (7) | 1.3 (7) |
| C29 | 0.868 (4) | 0.047 (1) | -0.1660 (8) | 2.9 (8) |

TABLE 1-continued

| Atom | X | Y | Z | B(A2) |
|---|---|---|---|---|
| C31 | 0.216 (4) | 0.271 (1) | −0.3066 (9) | 3.6 (9) |
| O112 | 0.185 (4) | −0.202 (1) | 0.1087 (8) | 10.1 (10) |
| O113 | 0.068 (4) | −0.130 (1) | 0.0768 (9) | 13.4 (12) |
| O111 | 0.465 (3) | −0.1962 (9) | 0.1084 (7) | 6.9 (8) |
| C92 | 0.104 (4) | −0.013 (1) | −0.057 (1) | 6.5 (12) |
| C94 | −0.058 (6) | −0.051 (2) | −0.021 (1) | 10.1 (16) |
| N101 | 0.911 (4) | 0.213 (1) | −0.010 (1) | 10.1 (13) |
| N91 | −0.006 (4) | 0.013 (1) | −0.0472 (9) | 6.9 (10) |
| C102 | 0.804 (7) | 0.227 (2) | −0.028 (2) | 17.0 (25) |
| O92 | 0.195 (3) | 0.012 (1) | −0.0740 (8) | 9.2 (10) |
| C95 | −0.138 (6) | −0.008 (2) | −0.029 (1) | 12.5 (19) |
| C93 | 0.083 (5) | −0.062 (2) | −0.040 (1) | 9.7 (16) |
| C103 | 0.702 (6) | 0.239 (2) | −0.048 (1) | 10.7 (16) |
| C96 | −0.037 (7) | 0.067 (2) | −0.055 (2) | 15.5 (23) |

The following coordinates represent one of the NMPO solvent molecules and a side chain phenyl group of molecule A.

TABLE 2

| Atom | X | Y | Z | B(A2) |
|---|---|---|---|---|
| C84 | 0.649 | −0.376 | 0.129 | 10.0 |
| N81 | 0.756 | −0.306 | 0.131 | 7.9 |
| O82 | 0.630 | −0.254 | 0.152 | 4.8 |
| C83 | 0.557 | −0.340 | 0.139 | 5.1 |
| C85 | 0.802 | −0.350 | 0.118 | 7.7 |
| C82 | 0.630 | −0.295 | 0.138 | 15.3 |
| C86 | 0.878 | −0.279 | 0.117 | 10.5 |
| C46' | 0.735 | −0.223 | 0.029 | 10.5 |
| C51' | 0.843 | −0.247 | 0.008 | 10.5 |
| C47' | 0.625 | −0.248 | 0.046 | 10.5 |
| C48' | 0.609 | −0.297 | 0.040 | 10.5 |
| C50' | 0.826 | −0.295 | 0.003 | 10.5 |
| C49' | 0.705 | −0.321 | 0.016 | 10.5 |

EXAMPLE 2

Conversion of Form D to Form A

A sample of the NMPO-solvated paclitaxel of Example 1 was further dried under high vacuum at 82° C. for 16 hours to give a material containing 0.05 molar equivalents of NMPO and shown to be Form A by X-ray powder diffraction.

EXAMPLE 3

Paclitaxel Purification

A crude taxane mixture containing 10.66 g of paclitaxel (paclitaxel area % at 227 nm=56) existed as a solution in 1.055 L of a solvent mixture consisting of a 2:1:1 (v:v:v) ratio of NMPO/acetonitrile/0.1% acetic acid. The solution was warmed to 40° C. with stirring and then, over a period of 80 minutes, a 0.1% aqueous acetic acid solution (520 mL in 4 portions) was added with seeding. After holding at 40° C. for 30 minutes, the slurry was allowed to cool to 20° C. over 90 minutes, then held at 20° C. for 30 minutes. The slurry was then heated to 58° C., stirred for 30 minutes and allowed to cool to 20° C. over 90 minutes. The slurry was stirred at 20° C. for 30 minutes followed by heating back to 58° C. After reaching 58° C. another addition of 0.1% aqueous acetic acid was made (520 mL) in one portion. A temperature oscillation cycle was then performed as follows:

Set point 1=58° C.; period 1=45 minutes.
Set point 2=58° C.; period 2=180 minutes.
Set point 3=20° C.; period 3=30 minutes.
Set point 4=20° C.

followed by holding at the final temperature of 20° C. The slurry was then stirred for 4 hours and filtered and washed successively with 80 mL each of 25% acetonitrile in 0.1% aqueous acetic acid and then 0.1% aqueous acetic acid and dried.

The dried cake yielded 13.47 g of material containing 10.52 g of crystalline paclitaxel solvate. The ratio of NMPO to paclitaxel was 1.0 to 1 by 1H NMR. The paclitaxel area % at 227 nm for the product was 92. The paclitaxel area % at 227 nm for the mother liquor was 9.5.

EXAMPLE 4

Paclitaxel Solvate Form E (DMF)

252 mg of paclitaxel was dissolved in 12.5 mL of DMF and 6.25 mL of $CH_3CN$ and stirred at 20° C. 6.25 mL of 0.1% acetic acid was added in 1 portion. The solution was stirred with heating to 40° C. and another 12.5 mL of 0.1% aqueous acetic acid was added in three portions over one minute. The solution was held at 40° C. for 1 hour, at which time no crystals were observed. The mixture was cooled with minimal stirring to 20° C. over 90 minutes, at which point a slurry was observed to form, and held at 20° C. for 1 hour. Thereafter the mixture was heated to 58° C. over 30 minutes to thin the slurry. The mixture was held at 58° C. for 30 minutes, with stirring, then cooled to 20° C. over 90 minutes. After being held at 20° C. for 16 hours (during which time the slurry thickens), the mixture was heated to 58° C. with stirring (and the slurry was observed to thin). The slurry was held at 58° C. for 1 hour. Then 12.5 mL of 0.1% acetic acid was added in 3 portions over 1 minute, at which point the slurry became dramatically thicker. The slurry was stirred at 58° C. for 30 minutes, then cooled to 20° C. over 3 hours and held at 20° C. with stirring. A little settling of the slurry was observed (about 20%). About 2 mL of the slurry was removed and filtered over about 5 minutes. The filter cake was washed in 25% $CH_3CN$/0.1% acetic acid (2 mL) and then dried under high vacuum at 40° C. for 16 hours to yield 210.0 mg solid. The mole ratio of DMF to paclitaxel as measured by 1H NMR spectroscopy was about 0.5:1.0 consistent with the single crystal structure of form E.

Single crystals of Form E DMF solvate (needles) had the following unit cell parameters at −53° C.:

Cell dimensions:
  a=9.512(1) Å
  b=27.787(4) Å
  c=34.788(5) Å

Volume: 9,195 Å$^3$

Space Group: P $2_1$ $2_1$ $2_1$ orthorhombic

Ideal composition of the unit cell: 8 paclitaxel, 4 DMF, 8 $H_2O$

Density (calculated): 1.312 g/cm$^3$

Figure 5:
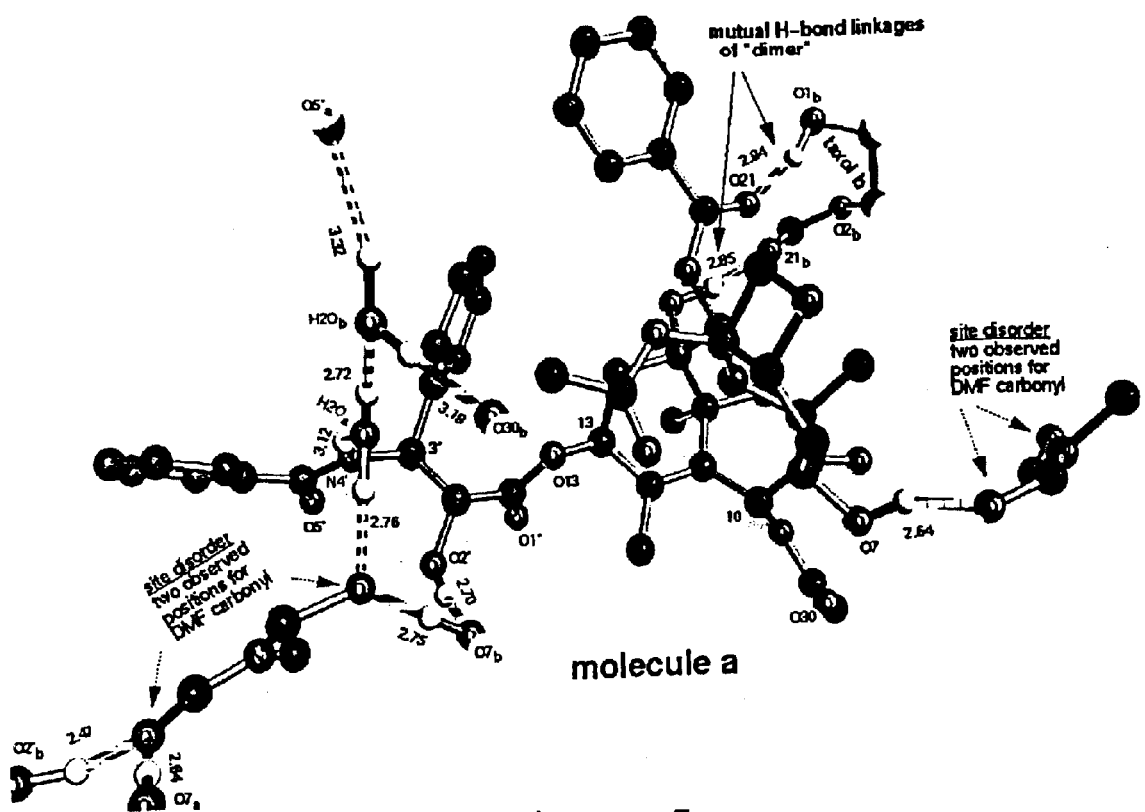
FIG. 5 is a depiction of the solid state arrangement of paclitaxel and solvent molecules in one part of the Form E solvate, based on the observed atomic coordinates.
Figure 6:
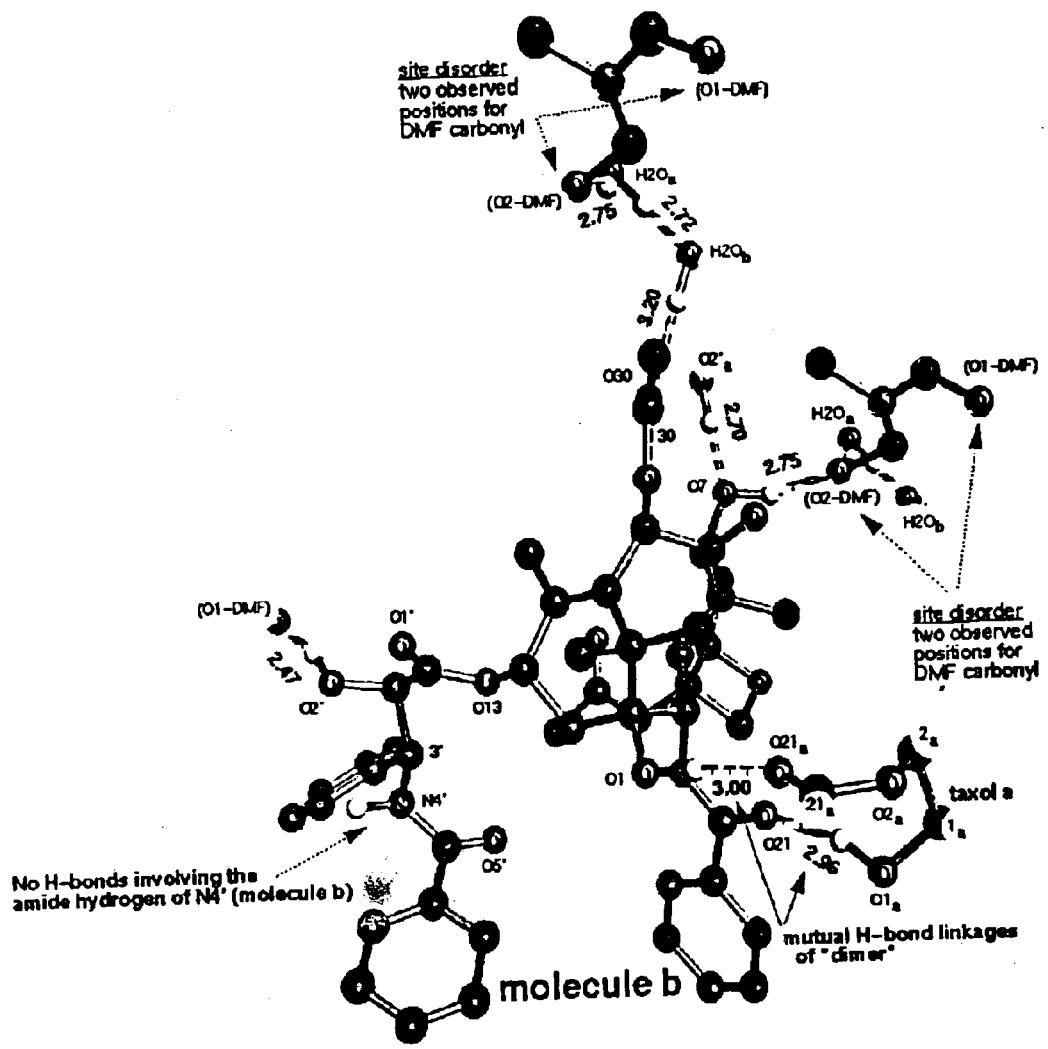
FIG. 6 is a depiction of the solid state arrangement of symmetry-independent paclitaxel and solvent molecules in another part of the Form E solvate, based on the observed atomic coordinates.

The unique arrangements of paclitaxel and solvent molecules in Form E are illustrated in FIGS. 5 and 6, based on the fractional atomic coordinates listed in Table 3 below. Except for some slight natural lattice expansion, the crystal structure remains the same under ambient conditions. The approximate coordinates in Table 3 herein therefore will vary according to the temperature at measurement. Statistical variations in these coordinates may also occur consistent with the reported error values.

TABLE 3

| Atom | X | Y | Z |
|---|---|---|---|
| C15 | 0.5181(7) | 0.4318(2) | −0.1705(2) |
| C17 | 0.3753(8) | 0.4393(2) | −0.1463(2) |
| C22 | 1.0541(8) | 0.4133(3) | −0.0894(2) |
| C24 | 1.1654(15) | 0.3472(5) | −0.0555(4) |
| C26 | 1.2480(12) | 0.4297(5) | −0.0452(3) |
| C27 | 1.1484(9) | 0.4461(3) | −0.0704(2) |
| C31 | 0.2362(10) | 0.4605(4) | −0.3026(3) |
| C1' | 0.3882(12) | 0.2588(3) | −0.1313(2) |
| O1' | 0.2716(8) | 0.2748(2) | −0.1316(2) |
| O5' | 0.7170(6) | 0.2745(2) | −0.0631(2) |
| N4' | 0.5110(7) | 0.2340(2) | −0.0591(2) |
| C5' | 0.6083(10) | 0.2668(3) | −0.0462(2) |
| C6' | 0.5694(8) | 0.2947(3) | −0.0108(2) |
| C17' | 0.6503(14) | 0.1250(4) | −0.1024(3) |
| C10' | 0.6185(12) | 0.3619(3) | 0.0302(3) |
| C7' | 0.4687(11) | 0.2814(3) | 0.0139(3) |
| C3' | 0.5409(10) | 0.2035(3) | −0.0918(2) |
| C12' | 0.5667(10) | 0.1506(3) | −0.0801(3) |
| O10 | 0.3932(5) | 0.4342(2) | −0.2556(2) |
| C19 | 0.9021(8) | 0.4486(3) | −0.2460(2) |
| C7 | 0.8025(8) | 0.3678(3) | −0.2726(2) |
| O7 | 0.7601(6) | 0.3836(2) | −0.3087(2) |
| O28 | 0.8041(7) | 0.2715(2) | −0.2104(2) |
| C23 | 1.0637(10) | 0.3650(4) | −0.0819(3) |
| C25 | 1.2601(12) | 0.3811(5) | −0.0379(3) |
| C11' | 0.6469(11) | 0.3348(3) | −0.0048(3) |
| C15' | 0.6177(20) | 0.0558(4) | −0.0623(6) |
| C9' | 0.5143(13) | 0.3473(4) | 0.0541(3) |
| C14' | 0.5250(18) | 0.0826(5) | −0.0367(4) |
| C8' | 0.4355(11) | 0.3099(4) | 0.0462(3) |
| C16' | 0.6829(16) | 0.0731(5) | −0.0929(4) |
| C16 | 0.5505(7) | 0.4826(2) | −0.1869(2) |
| O1 | 0.6465(4) | 0.4443(1) | −0.1114(1) |
| C1 | 0.6357(7) | 0.4131(2) | −0.1438(2) |
| O9 | 0.6431(6) | 0.4677(2) | −0.2716(2) |
| C9 | 0.6469(8) | 0.4316(3) | −0.2514(2) |
| O2 | 0.8821(4) | 0.4002(1) | −0.1358(1) |
| C21 | 0.9594(7) | 0.4337(3) | −0.1179(2) |
| C2 | 0.7825(6) | 0.4155(2) | −0.1648(2) |
| C28 | 0.8611(9) | 0.2745(3) | −0.1803(2) |
| C29 | 0.8698(11) | 0.2383(3) | −0.1500(3) |
| O13 | 0.5052(5) | 0.2848(1) | −0.1402(1) |
| C2' | 0.4244(10) | 0.2070(3) | −0.1223(2) |
| O2' | 0.3007(7) | 0.1845(2) | −0.1076(2) |
| C18 | 0.4370(8) | 0.3070(2) | −0.2168(2) |
| O30 | 0.4016(10) | 0.3983(3) | −0.3114(2) |
| C30 | 0.3435(10) | 0.4274(4) | −0.2923(3) |
| C10 | 0.5059(8) | 0.4050(2) | −0.2426(2) |
| C11 | 0.4893(7) | 0.3932(2) | −0.2004(2) |
| C12 | 0.4714(8) | 0.3461(3) | −0.1898(3) |
| C13 | 0.4820(8) | 0.3357(2) | −0.1475(2) |
| C14 | 0.6040(7) | 0.3628(2) | −0.1278(2) |
| C8 | 0.7913(7) | 0.4089(2) | −0.2405(2) |
| C3 | 0.8009(6) | 0.3818(2) | −0.2020(2) |
| O21 | 0.9509(5) | 0.4761(2) | −0.1253(1) |
| O4 | 0.9252(5) | 0.3149(2) | −0.1704(2) |
| C6 | 0.9464(8) | 0.3465(3) | −0.2752(2) |
| O5 | 1.1373(5) | 0.3678(2) | −0.2279(2) |
| C4 | 0.9412(8) | 0.3531(2) | −0.1991(2) |
| C20 | 1.0812(8) | 0.3794(3) | −0.1906(2) |
| C5 | 1.0144(9) | 0.3344(3) | −0.2356(2) |
| C13' | 0.5006(13) | 0.1304(4) | −0.0474(3) |
| C43 | 0.8809(6) | 0.6438(2) | −0.2016(2) |
| C45 | 0.6695(8) | 0.6906(3) | −0.2388(2) |
| C46 | 0.7522(9) | 0.6828(3) | −0.2765(2) |
| C49 | 1.0427(8) | 0.5963(3) | −0.2512(2) |
| C55 | 1.1585(7) | 0.5926(2) | −0.1670(2) |
| C57 | 1.2951(7) | 0.5844(2) | −0.1420(2) |
| C58 | 1.2564(7) | 0.7179(3) | −0.2092(2) |
| C60 | 0.5978(7) | 0.6441(3) | −0.1949(3) |
| C66 | 0.4412(9) | 0.5914(3) | −0.0428(2) |
| C65 | 0.4404(9) | 0.6411(4) | −0.0324(3) |
| C64 | 0.5279(11) | 0.6739(3) | −0.0507(3) |
| C69 | 0.7927(10) | 0.7875(3) | −0.1509(3) |
| C71 | 1.4484(9) | 0.5682(3) | −0.3008(3) |
| C41' | 1.2782(11) | 0.7650(3) | −0.1241(2) |
| C43' | 1.2300(9) | 0.8180(2) | −0.0692(2) |

TABLE 3-continued

| Atom | X | Y | Z |
|---|---|---|---|
| O49 | 1.0493(5) | 0.5605(2) | −0.2704(2) |
| C56' | 1.0693(13) | 0.7061(3) | −0.0234(3) |
| C52' | 1.1217(10) | 0.7833(3) | −0.0531(2) |
| N44' | 1.1992(8) | 0.8670(2) | −0.0558(2) |
| C45' | 1.2893(13) | 0.8950(4) | −0.0356(3) |
| C57' | 1.1634(10) | 0.7394(3) | −0.0371(2) |
| C54' | 0.8780(10) | 0.7566(3) | −0.0457(3) |
| C42 | 0.8925(7) | 0.6088(2) | −0.1656(2) |
| O45' | 0.5524(5) | 0.6576(2) | −0.2341(2) |
| O47 | 0.9403(6) | 0.6458(2) | −0.3093(2) |
| C47 | 0.8936(9) | 0.6621(3) | −0.2714(2) |
| O50 | 1.2954(5) | 0.5937(2) | −0.2519(2) |
| C70 | 1.3318(10) | 0.5990(3) | −0.2876(3) |
| C63 | 0.6178(8) | 0.6576(3) | −0.0799(2) |
| C59 | 0.7854(8) | 0.5800(3) | −0.2514(2) |
| C44 | 0.7370(8) | 0.6727(2) | −0.1996(2) |
| O68 | 0.8736(7) | 0.7538(2) | −0.2102(2) |
| O41' | 1.3962(8) | 0.7494(2) | −0.1225(2) |
| C49' | 1.1713(20) | 1.0251(4) | 0.0158(4) |
| C48' | 1.0938(17) | 1.0081(4) | −0.0154(4) |
| C53' | 0.9795(11) | 0.7921(3) | −0.0585(3) |
| C47' | 1.1375(15) | 0.9632(3) | −0.0334(3) |
| C50' | 1.2853(17) | 0.9993(5) | 0.0295(4) |
| C55' | 0.9280(14) | 0.7160(3) | −0.0286(3) |
| C51' | 1.3239(12) | 0.9565(4) | 0.0107(3) |
| C61 | 0.7121(7) | 0.5880(2) | −0.1203(2) |
| O61 | 0.7200(5) | 0.5470(2) | −0.1292(1) |
| C62 | 0.6189(7) | 0.6081(3) | −0.0889(2) |
| C67 | 0.5324(8) | 0.5741(3) | −0.0706(2) |
| O42 | 0.7871(5) | 0.6235(1) | −0.1381(1) |
| O44 | 0.7456(5) | 0.7085(2) | −0.1714(1) |
| C68 | 0.8102(9) | 0.7497(3) | −0.1803(2) |
| C42' | 1.2378(9) | 0.8158(2) | −0.1127(2) |
| O42' | 1.3458(7) | 0.8475(2) | −0.1253(2) |
| C52 | 1.2129(7) | 0.6778(2) | −0.1834(2) |
| C53 | 1.1895(7) | 0.6875(2) | −0.1418(2) |
| O53 | 1.1648(5) | 0.7385(1) | −0.1348(1) |
| C54 | 1.0635(7) | 0.6614(2) | −0.1257(2) |
| C41 | 1.0334(6) | 0.6107(2) | −0.1430(2) |
| C51 | 1.1903(7) | 0.6320(2) | −0.1965(2) |
| O41 | 1.0162(4) | 0.5785(1) | −0.1105(1) |
| C56 | 1.1285(7) | 0.5428(2) | −0.1855(2) |
| C50 | 1.1793(8) | 0.6218(2) | −0.2389(2) |
| O70 | 1.2637(12) | 0.6258(2) | −0.3085(2) |
| O45 | 1.4073(13) | 0.8794(2) | −0.0307(2) |
| C46' | 1.2515(13) | 0.9385(3) | −0.0202(2) |
| C48 | 0.8968(7) | 0.6188(2) | −0.2423(2) |
| N125 | 0.7714(10) | 0.5174(3) | −0.3682(3) |
| C126 | 0.7315(13) | 0.5631(5) | −0.3764(4) |
| C127 | 0.8863(16) | 0.5059(5) | −0.3584(4) |
| C128 | 0.6543(13) | 0.4804(4) | −0.3756(4) |
| O131 | 0.9302(9) | 0.9017(3) | −0.0990(3) |
| O132 | 0.6429(16) | 0.9026(5) | −0.0976(4) |
| O129 | 0.9125(9) | 0.4519(3) | −0.3483(3) |
| O130 | 0.7787(23) | 0.6069(8) | −0.3632(7) |

EXAMPLE 5

DMAC Solvate of Paclitaxel 250 mg of paclitaxel was dissolved in 12.5 mL of DMAC and 6.25 ml of acetonitrile and stirred at 20° C. 6.25 mL of 0.1% acetic acid was added and the resulting mixture was heated to 40° C. An additional 12.5 mL of 0.1% acetic acid solution was added in three portions over one minute and the resulting mixture was held at 40° C. for one hour, at which point precipitation was observed to begin. The mixture was cooled with minimal agitation to 20° C. over 90 minutes and held at this temperature for one hour, at the end of which time the mixture was a thick slurry. The slurry was then heated to 58° C. over 30 minutes and held at this temperature for another 30 minutes with stirring, and the slurry was observed to thin. The thinned slurry was cooled to 20° C.

over 90 minutes and held at 20° C. for 16 hours. The resulting mixture was heated to 58° C., with stirring. Some settling was observed. The slurry was held at 58° C. for 1 hour. 12.5 mL of 0.1% acetic acid was added in three portions over 1 minute. The slurry was held at 58° C. for another 30 minutes. The mixture was cooled to 20° C. over 3 hours and held at that temperature with stirring. After about 10 days, 80% of the mixture had settled. 2 mL of slurry was removed, filtered quickly and washed with 2 mL of a solution of 25% acetonitrile and 0.1% acetic acid. A solid of unknown structure was obtained. However, 1H NMR spectroscopy showed a molar ratio of DMAC to paclitaxel of 1.0:1.0. The appearance of this amount of solvent in the solid after washing suggested that a crystalline solvate was formed.

EXAMPLE 6

DMSO Solvate of Paclitaxel 253 mg of paclitaxel was dissolved in 12.5 mL of DMSO and 6.25 mL of $CH_3CN$ and 6.25 mL of 0.1% aqueous acetic acid solution. The resulting mixture was heated to 40° C. and an additional 12.5 mL of 0.1% acetic acid was added. The mixture was held at 40° C. for 30 minutes and significant precipitation was observed. The slurry was cooled to 20° C. over 90 minutes and stirred at 20° C. for 1 hour. The slurry was then heated to 58° C. over 30 minutes and held at 58° C. for 30 minutes, stirred rapidly for 5 minutes and then cooled to 20° C. over 3 hours and held at 20° C. for 30 minutes. The solution was again heated to 58° C. for 30 minutes and held at that temperature for 30 minutes, and then stirred rapidly for 5 minutes. The solution was heated briefly to 67° C. and 12.5 mL of 0.1% aqueous acetic acid added. The solution was then allowed to cool to 20° C. over 3 hours and then held at 20° C. for 18 hours. After precipitation was observed to be complete, some settling (about 20% to 30%) was observed. The slurry was filtered over filter paper and washed with 2 mL of 25% $CH_3CN$/0.1% acetic acid. The filter cake was dried under high vacuum at 40° C. for 18 hours, yielding 230 mg of a solid of unknown structure. However, upon analysis by 1H NMR, the molar ratio of DMSO to paclitaxel was determined to be about 1.3:1. The appearance of this amount of solvent in the solid after washing suggested that a crystalline solvate was formed.

EXAMPLE 7

DMPU Solvate of Paclitaxel 258 mg of paclitaxel was dissolved in 12.5 mL of DMPU, 6.25 mL of $CH_3CN$ and 6.25 mL of 0.1% acetic acid. An additional 12.5 mL of. 0.1% acetic acid was added. The temperature oscillation protocol described in Example 1 above was performed. After a hold time of between 10 and 20 hours, the slurry was assayed and precipitation determined to be complete. No settling was observed. The slurry was filtered over 15 minutes and washed in 3 mL of a 0.1% acetic acid/25% $CH_3CN$ solution. The filter cake was dried under high vacuum at 40° C. for 18 hours to yield 235 mg of solid of unknown structure. However, 1H NMR spectroscopy showed a molar ratio of DMPU:paclitaxel of about 1.0:1.0. The appearance of this amount of solvent in the solid suggested the formation of a crystalline solvate.

Comparative Example 1

A 1.062 g sample of crude paclitaxel material was dissolved in 4 ml acetone and precipitation was performed with the addition of 0.1% aqueous acetic acid to the cloud point substantially in accordance with the above-described methods. The mixture was warmed and cooled periodically and more acetone (2 mL) and water were added. Precipitation was observed to proceed slowly. The mixture was stirred overnight (16 hours) and the material decanted. HPLC analysis determined that the purity of the precipitate was not increased to the same degree as when crystallization was performed with an amidic organic solvent or DMSO. By microscopic examination, acicular crystals were observed, but were not further characterized or examined for solvent content. However, it is noted that a relatively low solvent:paclitaxel ratio of 1:10 was observed by 1H NMR analysis when pure paclitaxel and acetone were used according to the procedure of Examples 1 or 4–7.

EXAMPLE 8

Cytotoxicity

Figure 7:
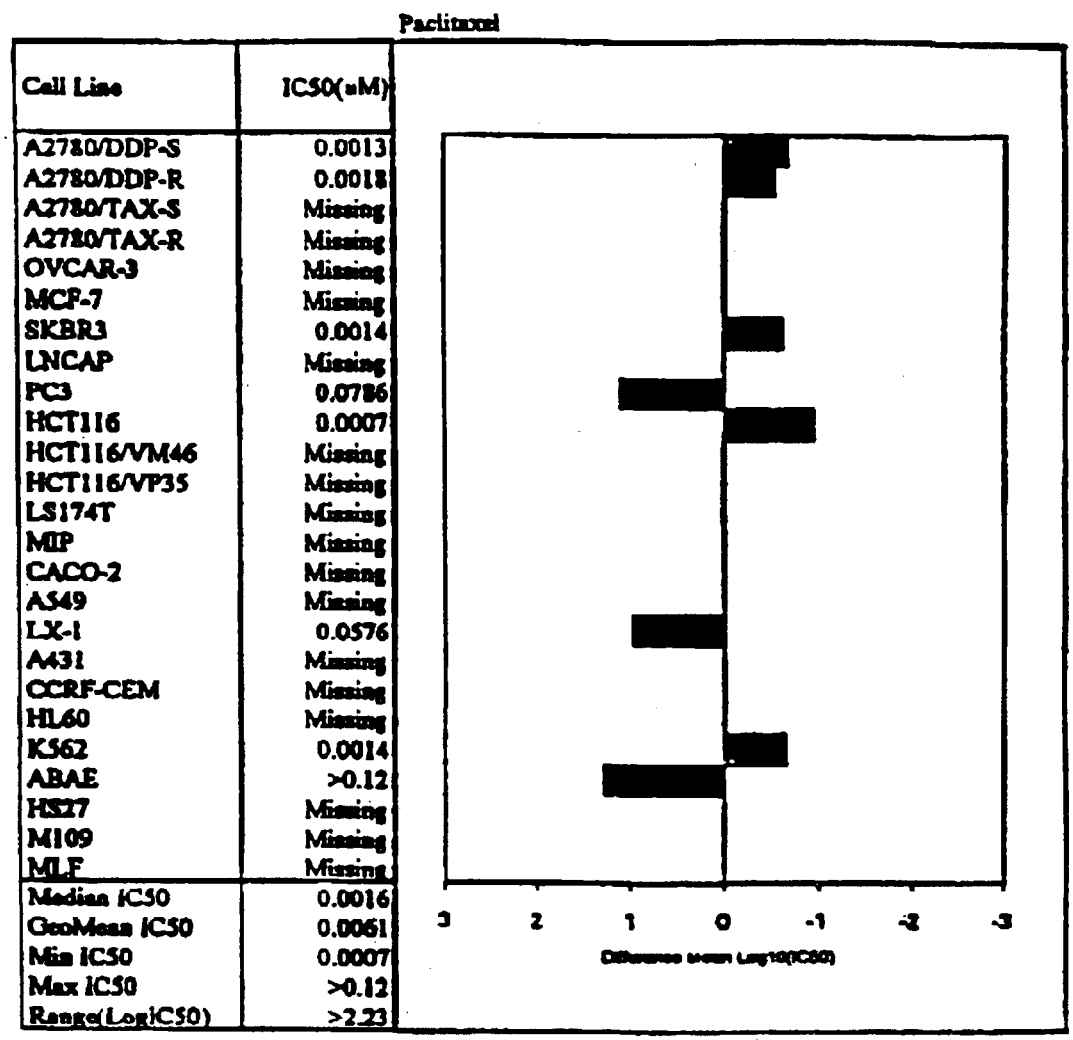
FIG. 7 is a tabular representation of cytotoxicity ($IC_{50}$ values) obtained for paclitaxel.
Figure 8:
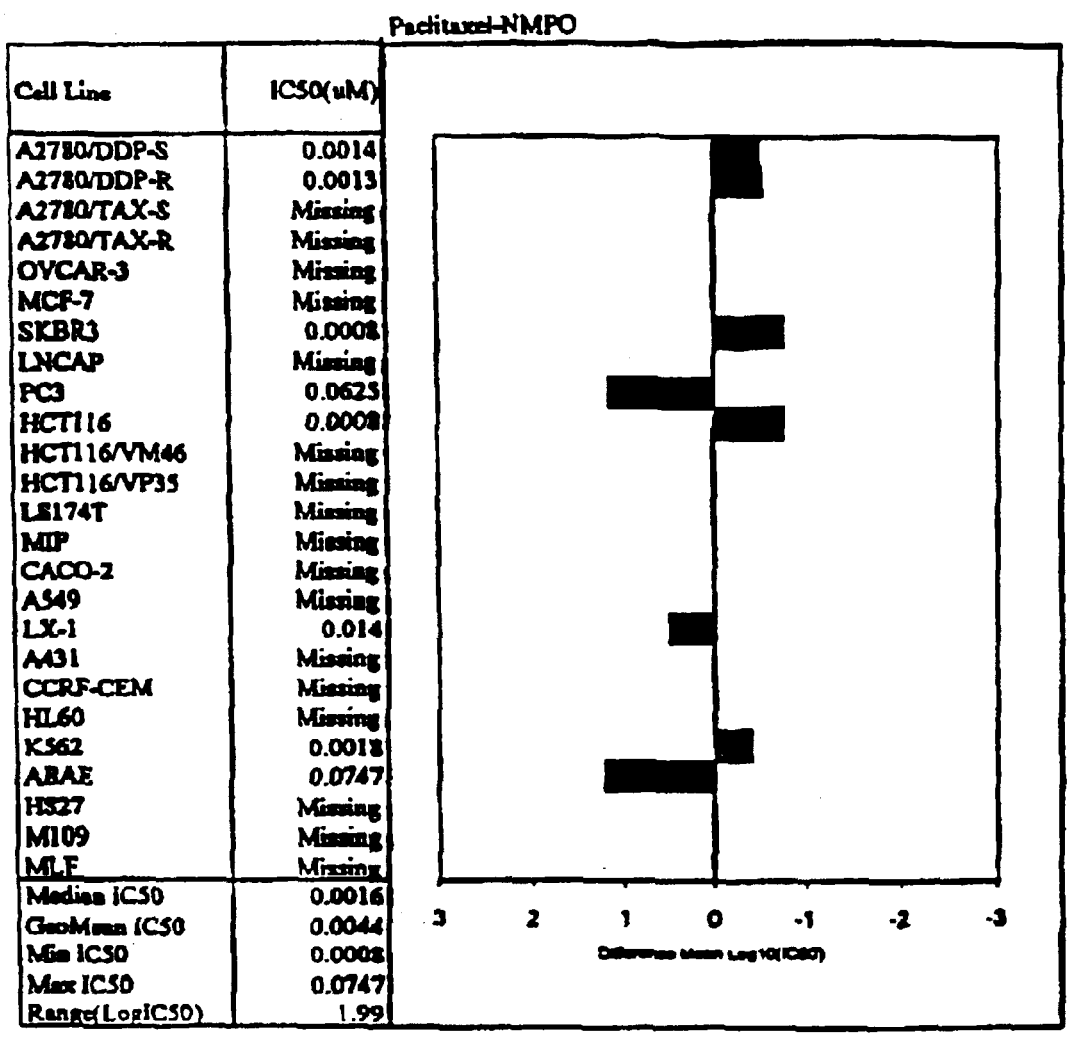
FIG. 8 is a tabular representation of cytotoxicity ($IC_{50}$ values) obtained for a paclitaxel NMPO solvate prepared according to the invention.

Cytotoxicity of the NMPO solvate of Example 1 was assessed in cell lines by MTS (3-(4,5-dimethylthiazol-2-yl)-5-(3-carboxymethoxyphenyl)-2-(4-sulphenyl-2H-tetrazolium, inner salt) assay as reported in T. L. Riss, et al., "Comparison of MTT, XTT, and a Novel Tetrazolium Compound MTS for in vitro Proliferation and Chemosensitivity Assays.," Mol. Biol. Cell 3 (Suppl.):184a, 1992. Cells were plated at 4,000 cell/well in 96 well microtiter plates and 24 hours later drugs were added and serial diluted. The cells were incubated at 37° C. for 72 hours at which time the tetrazolium dye, MTS at 333 $\mu$g/mL (final concentration), in combination with the electron coupling agent phenazine methosulfate at 25 $\mu$M (final concentration) was added. A dehydrogenase enzyme in live cells reduces the MTS to a form that absorbs light at 492 nm, which can be quantitated spectrophotometrically. The greater the absorbance, the greater the number of live cells. The results are expressed as an IC50, which is the drug concentration required to inhibit cell proliferation (i.e., absorbance at 450 nm) to 50% of that of untreated control cells. The data represented in FIG. 7 and FIG. 8 show the comparable biological activity in vitro of a paclitaxel solvate of NMPO and paclitaxel.

What is claimed is:

1. A crystalline solvate comprising paclitaxel and a solvent selected from the group consisting of dimethylsulfoxide, N,N'-dimethylformamide, N,N'-dimethylacetamide, N-methyl-2-pyrrolidone, 1,3-dimethyl-2-imidazolidinone, 1,3-dimethyl-3,4,5,6-tetrahydro-2-(1H)-pyrimidinone, and acetonitrile and combinations thereof, and optionally alos including water.

2. The solvate of claim 1, wherein said solvents are N-methyl-2-pyrrolidone and acetonitrile.

3. The solvate of claim 1, which comprises about three molecules of water, about two molecules of N-methyl-2-pyrrolidone, and about one molecule of acetonitrile per two molecules of paclitaxel.

4. The solvate of claim 1, wherein said solvent is N,N'-dimethylformamide.

5. The solvate of claim 4, which comprises about one molecule of N,N'-dimethylformamide per two molecules of paclitaxel.

6. The solvate of claim 1, wherein said solvent is N,N'-dimethylacetamide.

7. The solvate of claim 6, which comprises about one molecule of N,N'-dimethylacetamide per one molecule of paclitaxel.

8. The solvate of claim 1, wherein said solvent is 1,3-dimethyl-3,4,5,6-tetrahydro-2-(1H)-pyrimidinone.

9. The solvate of claim 1, which comprises about one molecule of 1,3-dimethyl-3,4,5,6-tetrahydro-2-(1H)-pyrimidinone per one molecule of paclitaxel.

10. The solvate of claim 1, wherein said solvent is dimethylsulfoxide.

11. The solvate of claim 10, which comprises about 1–2 molecules of dimethylsulfoxide per molecule of paclitaxel.

12. A form D crystalline paclitaxel solvate according to claim 1.

13. A form D crystalline paclitaxel solvate according to claim 3.

14. A form E crystalline paclitaxel solvate according to claim 1.

15. A form E crystalline paclitaxel solvate according to claim 5.

16. A method for the preparation of paclitaxel which comprises converting the crystalline solvate of claim 1 into Form A paclitaxel.

17. The method of claim 16, wherein the conversion comprises desolvating the solvate under vacuum at an elevated temperature to obtain Form A paclitaxel.

18. A method for the preparation of crystalline paclitaxel solvates comprising:
   a) forming a mixture of:
      (i) a paclitaxel-containing material; and
      (ii) one or more organic solvents, each said solvent having solvent molecules compatible with solvent sites in the crystalline arrangement of the solvate; and
   b) removing solvent from the mixture to recover a solid, crystalline paclitaxel solvate having paclitaxel and solvent molecules within the crystal structure.

19. The method of claim 18 wherein each said solvent is an aqueous solution of an organic solvent.

20. The method of claim 19 wherein the organic solvent is selected from the group consisting of dimethylsulfoxide, N,N'-dimethylformamide, N,N'-dimethylacetamide, N-methyl-2-pyrrolidone, 1,3-dimethyl-2-imidazolidinone, 1,3-dimethyl-3,4,5,6-tetrahydro-2-(1H)-pyrimidinone, and acetonitrile and combinations thereof.

21. The method of claim 18 wherein the crystalline paclitaxel solvate comprises a dimer composed of about two molecules of paclitaxel and from about 0.5 to about 2 molecules of the organic solvent.

22. The method of claim 18 further comprising subjecting the mixture of step (a) to a temperature oscillation before initiating step (b).

23. A crystalline paclitaxel solvate formed according to the method of claim 18.

24. A crystalline paclitaxel solvate formed according to the method of claim 20.

25. A crystalline paclitaxel solvate formed according to the method of claim 20, which is composed of about two molecules of paclitaxel, about 3 molecules of water, about 2 molecules of N-methyl-2-pyrrolidone and about one molecule of acetonitrile.

26. A crystalline paclitaxel solvate formed according to the method of claim 20, which is composed of about two molecules of paclitaxel, about two molecules of water and about one molecule of N,N'-dimethylformamide.

27. A crystalline solvate of paclitaxel consisting essentially of about two molecules of paclitaxel, about 3 molecules of water, about 2 molecules of N-methyl-2-pyrrolidone and about one molecule of acetonitrile.

28. A crystalline solvate of paclitaxel consisting essentially of about two molecules of paclitaxel, about two molecules of water and about one molecule of N,N'-dimethylformamide.

29. A method for processing a paclitaxel-containing material to obtain paclitaxel comprising:
   a) forming a mixture of:
      (i) a paclitaxel-containing material, and
      (ii) an aqueous solution comprising one or more organic solvents; and
   b) removing solvent from the mixture to isolate a crystalline paclitaxel solvate; and
   c) desolvating the crystalline solid.

30. The method of claim 29 wherein in step (c) the crystalline solvate is heated.

31. The method of claim 29 wherein in step (b), the mixture is subjected to temperature oscillation.

32. The method of claim 29 wherein in step (a), an acidifying agent is added to the mixture.

33. Form D paclitaxel solvate having a crystalline arrangement composed of:
   a) paclitaxel molecules; and
   b) solvent molecules located in solvent sites within the crystalline structure.

34. Form E paclitaxel solvate having a crystalline arrangement composed of:
   a) paclitaxel molecules; and
   b) solvent molecules located in solvent sites within the crystalline structure.

35. An orthorhombic paclitaxel solvate crystal containing a solvent, which is characterized by unit cell parameters a of about 9.54 Å, b of about 28.46 Å, and c of about 37.24 Å; and a space group symmetry p $2_1\, 2_1\, 2_1$; the crystal consisting of eight paclitaxel molecules in an arrangement and conformations according to the fractional atomic coordinates expressed in Table 1:

TABLE 1

| Atom | X | Y | Z | B(A2) |
|---|---|---|---|---|
| C44 | 0.219 (3) | 0.0264 (9) | 0.2022 (7) | 1.2 (7) |
| C41 | 0.517 (3) | 0.092 (1) | 0.1537 (7) | 1.6 (7) |
| C48 | 0.384 (3) | 0.072 (1) | 0.2427 (7) | 1.9 (7) |
| C55 | 0.653 (4) | 0.108 (1) | 0.1774 (8) | 2.3 (8) |
| C51 | 0.681 (4) | 0.063 (1) | 0.2022 (9) | 3.4 (9) |
| C62 | 0.098 (4) | 0.099 (1) | 0.1032 (8) | 3.6 (9) |
| C52' | 0.573 (3) | −0.076 (1) | 0.0594 (7) | 1.7 (7) |
| C49 | 0.526 (4) | 0.098 (1) | 0.2529 (8) | 2.1 (8) |
| C61 | 0.198 (4) | 0.115 (1) | 0.1297 (8) | 2.4 (8) |
| C41' | 0.758 (4) | −0.058 (1) | 0.1229 (8) | 2.7 (8) |
| C45' | 0.768 (5) | −0.172 (1) | 0.038 (1) | 7.9 (14) |
| C52 | 0.701 (3) | 0.0231 (9) | 0.1857 (7) | 1.1 (7) |
| C68 | 0.295 (4) | −0.050 (1) | 0.1792 (8) | 2.1 (8) |
| C70 | 0.840 (4) | 0.088 (1) | 0.287 (1) | 5.6 (11) |
| C43 | 0.368 (3) | 0.0519 (9) | 0.2045 (7) | 0.5 (6) |
| C50 | 0.665 (3) | 0.071 (1) | 0.2403 (8) | 2.1 (8) |
| C42 | 0.368 (3) | 0.0920 (9) | 0.1747 (7) | 0.4 (6) |
| C43' | 0.689 (3) | −0.1076 (9) | 0.0705 (7) | 0.9 (7) |
| C53 | 0.687 (3) | 0.019 (1) | 0.1454 (8) | 2.4 (8) |
| C45 | 0.157 (3) | 0.005 (1) | 0.2369 (8) | 2.4 (8) |
| C42' | 0.712 (4) | −0.108 (1) | 0.1154 (8) | 2.5 (8) |
| C47 | 0.376 (3) | 0.031 (1) | 0.2696 (8) | 2.1 (7) |
| C63 | 0.087 (4) | 0.049 (1) | 0.0956 (9) | 4.9 (10) |
| C67 | 0.033 (3) | 0.136 (1) | 0.0854 (7) | 1.6 (7) |
| C57' | 0.441 (4) | −0.090 (1) | 0.0602 (9) | 4.8 (10) |
| C53' | 0.613 (4) | −0.031 (1) | 0.046 (1) | 5.8 (11) |
| C64 | −0.020 (4) | 0.036 (1) | 0.0694 (9) | 4.9 (11) |
| C66 | −0.074 (4) | 0.122 (1) | 0.0603 (8) | 3.4 (9) |
| C54' | 0.498 (4) | 0.001 (1) | 0.0377 (8) | 2.6 (8) |
| C56' | 0.334 (4) | −0.061 (1) | 0.051 (1) | 5.1 (11) |
| C65 | −0.088 (4) | 0.074 (1) | 0.052 (1) | 5.0 (10) |
| C55' | 0.362 (4) | −0.014 (1) | 0.0372 (8) | 2.7 (8) |
| O44 | 0.235 (2) | −0.0071 (7) | 0.1735 (5) | 2.3 (5) |
| O50 | 0.779 (2) | 0.0972 (7) | 0.2539 (5) | 3.3 (5) |
| O42 | 0.277 (2) | 0.0788 (6) | 0.1461 (4) | 1.0 (4) |

TABLE 1-continued

| Atom | X | Y | Z | B(A2) |
|---|---|---|---|---|
| O53 | 0.646 (2) | −0.0335 (6) | 0.1366 (5) | 1.8 (5) |
| O45 | 0.036 (2) | 0.0369 (7) | 0.2317 (5) | 3.4 (6) |
| O49 | 0.544 (2) | 0.1271 (8) | 0.2745 (5) | 3.5 (6) |
| O61 | 0.211 (2) | 0.1540 (6) | 0.1434 (5) | 1.0 (4) |
| O41' | 0.872 (3) | −0.0418 (7) | 0.1206 (6) | 3.9 (6) |
| O45' | 0.855 (2) | −0.156 (1) | 0.0227 (7) | 8.6 (9) |
| O68 | 0.359 (2) | −0.0540 (7) | 0.2077 (5) | 3.3 (6) |
| O70 | 0.802 (3) | 0.0504 (8) | 0.2991 (6) | 5.1 (7) |
| N44' | 0.669 (3) | −0.1571 (9) | 0.0608 (7) | 3.5 (7) |
| C54 | 0.553 (3) | 0.0428 (9) | 0.1321 (7) | 0.7 (7) |
| C46 | 0.229 (4) | 0.010 (1) | 0.2720 (8) | 2.5 (8) |
| C60 | 0.084 (4) | 0.053 (1) | 0.1934 (8) | 3.0 (9) |
| O41 | 0.494 (2) | 0.1261 (6) | 0.1247 (5) | 1.2 (4) |
| O42' | 0.824 (2) | −0.1385 (7) | 0.1229 (5) | 2.5 (5) |
| O47 | 0.415 (2) | 0.0416 (7) | 0.3046 (5) | 2.6 (5) |
| C59 | 0.275 (4) | 0.113 (1) | 0.2549 (8) | 3.1 (9) |
| C56 | 0.615 (3) | 0.1548 (9) | 0.1965 (7) | 0.8 (7) |
| C57 | 0.788 (3) | 0.117 (1) | 0.1527 (7) | 1.5 (7) |
| C58 | 0.734 (3) | −0.023 (1) | 0.2075 (8) | 2.5 (8) |
| C69 | 0.298 (3) | −0.083 (1) | 0.1483 (8) | 2.2 (8) |
| C71 | 0.950 (4) | 0.120 (1) | 0.2981 (8) | 3.0 (8) |
| C4 | 0.946 (3) | 0.161 (1) | −0.2152 (8) | 2.0 (8) |
| C1 | 0.631 (3) | 0.2169 (9) | −0.1612 (7) | 1.1 (7) |
| C8 | 0.780 (4) | 0.212 (1) | −0.2543 (8) | 2.7 (8) |
| C15 | 0.508 (3) | 0.238 (1) | −0.1862 (8) | 1.7 (7) |
| C11 | 0.474 (4) | 0.199 (1) | −0.2140 (9) | 3.9 (9) |
| C22 | 1.052 (3) | 0.225 (1) | −0.1124 (7) | 1.1 (7) |
| C6' | 0.473 (3) | 0.099 (1) | −0.0287 (8) | 2.1 (8) |
| C12' | 0.573 (3) | −0.032 (1) | −0.0938 (8) | 2.5 (8) |
| C9 | 0.642 (4) | 0.235 (1) | −0.2626 (8) | 2.7 (8) |
| C21 | 0.953 (4) | 0.240 (1) | −0.1397 (8) | 3.2 (9) |
| C1' | 0.386 (3) | 0.0635 (9) | −0.1493 (7) | 0.6 (6) |
| C5' | 0.545 (4) | 0.075 (1) | −0.0630 (9) | 4.7 (10) |
| C12 | 0.466 (3) | 0.1535 (9) | −0.2038 (7) | 1.0 |
| C28 | 0.850 (4) | 0.080 (1) | −0.1952 (8) | 3.2 (9) |
| C30 | 0.325 (4) | 0.236 (1) | −0.301 (1) | 4.8 (10) |
| C3 | 0.788 (3) | 0.1857 (9) | −0.2161 (7) | 0.6 (6) |
| C10 | 0.491 (3) | 0.207 (1) | −0.2537 (8) | 1.7 (7) |
| C2 | 0.770 (4) | 0.222 (1) | −0.1823 (8) | 2.5 (8) |
| C3' | 0.535 (4) | 0.019 (1) | −0.1081 (8) | 2.3 (8) |
| C13 | 0.466 (4) | 0.1421 (9) | −0.1625 (7) | 1.0 |
| C5 | 1.011 (3) | 0.139 (1) | −0.2506 (8) | 2.4 (8) |
| C2' | 0.444 (3) | 0.014 (1) | −0.1411 (7) | 2.1 (8) |
| C7 | 0.787 (3) | 0.171 (1) | −0.2825 (7) | 2.0 (8) |
| C23 | 1.082 (3) | 0.175 (1) | −0.1095 (7) | 1.3 (7) |
| C27 | 1.134 (3) | 0.258 (1) | −0.0928 (8) | 2.0 (7) |
| C11' | 0.572 (4) | 0.127 (1) | −0.0072 (9) | 5.0 (10) |
| C7' | 0.342 (4) | 0.091 (1) | −0.0169 (8) | 3.3 (9) |
| C17' | 0.525 (4) | −0.049 (1) | −0.0606 (9) | 4.2 (10) |
| C13' | 0.657 (5) | −0.059 (1) | −0.114 (1) | 6.8 (12) |
| C26 | 1.238 (4) | 0.245 (1) | −0.0687 (8) | 3.0 (8) |
| C24 | 1.192 (4) | 0.162 (1) | −0.0871 (8) | 3.9 (10) |
| C8' | 0.286 (4) | 0.110 (1) | 0.0165 (9) | 4.3 (10) |
| C10' | 0.530 (5) | 0.142 (1) | 0.027 (1) | 7.1 (12) |
| C16' | 0.564 (4) | −0.091 (1) | −0.0481 (9) | 5.1 (11) |
| C14' | 0.697 (4) | −0.104 (1) | −0.1009 (9) | 5.2 (11) |
| C25 | 1.264 (4) | 0.195 (1) | −0.0635 (9) | 3.8 (9) |
| C9' | 0.393 (4) | 0.137 (1) | 0.0367 (9) | 3.9 (9) |
| C15' | 0.650 (4) | −0.120 (1) | −0.0677 (9) | 5.1 (11) |
| O4 | 0.923 (2) | 0.1233 (7) | −0.1868 (5) | 1.9 (5) |
| O10 | 0.380 (2) | 0.2383 (7) | −0.2634 (5) | 3.0 (5) |
| O2 | 0.880 (2) | 0.2052 (6) | −0.1559 (5) | 1.5 (4) |
| O13 | 0.503 (2) | 0.0934 (7) | −0.1594 (5) | 2.7 (5) |
| O5 | 1.122 (2) | 0.1722 (7) | −0.2426 (5) | 2.7 (5) |
| O9 | 0.629 (2) | 0.2698 (6) | −0.2812 (5) | 1.4 (4) |
| O21 | 0.930 (2) | 0.2810 (7) | −0.1445 (5) | 2.2 (5) |
| O1' | 0.272 (2) | 0.0783 (7) | −0.1498 (5) | 3.2 (5) |
| O5' | 0.665 (3) | 0.0900 (8) | −0.0721 (6) | 4.1 (6) |
| O28 | 0.791 (2) | 0.0807 (7) | −0.2238 (5) | 3.2 (6) |
| O30 | 0.371 (2) | 0.2020 (9) | −0.3153 (6) | 5.9 (7) |
| N4' | 0.460 (3) | 0.0444 (8) | −0.0782 (6) | 1.5 (6) |
| C14 | 0.599 (3) | 0.165 (1) | −0.1470 (7) | 1.5 (7) |
| C6 | 0.947 (3) | 0.151 (1) | −0.2854 (7) | 2.9 (9) |
| C20 | 1.078 (3) | 0.188 (1) | −0.2072 (7) | 1.9 (8) |
| O1 | 0.648 (2) | 0.2464 (6) | −0.1304 (5) | 1.3 (4) |
| O2' | 0.324 (2) | −0.0158 (7) | −0.1374 (5) | 2.5 (5) |
| O7 | 0.742 (2) | 0.1856 (6) | −0.3173 (5) | 1.9 (5) |

TABLE 1-continued

| Atom | X | Y | Z | B(A2) |
|---|---|---|---|---|
| C19 | 0.891 (3) | 0.253 (1) | −0.2590 (7) | 1.6 (7) |
| C16 | 0.543 (3) | 0.287 (1) | −0.2021 (7) | 1.3 (7) |
| C17 | 0.369 (3) | 0.243 (1) | −0.1634 (7) | 1.4 (7) |
| C18 | 0.433 (3) | 0.113 (1) | −0.2291 (7) | 1.3 (7) |
| C29 | 0.868 (4) | 0.047 (1) | −0.1660 (8) | 2.9 (8) |
| C31 | 0.216 (4) | 0.271 (1) | −0.3066 (9) | 3.6 (9) |
| O112 | 0.185 (4) | −0.202 (1) | 0.1087 (8) | 10.1 (10) |
| O113 | 0.068 (4) | −0.130 (1) | 0.0768 (9) | 13.4 (12) |
| O111 | 0.465 (3) | −0.1962 (9) | 0.1084 (7) | 6.9 (8) |
| C92 | 0.104 (4) | −0.013 (1) | −0.057 (1) | 6.5 (12) |
| C94 | −0.058 (6) | −0.051 (1) | −0.021 (1) | 10.1 (16) |
| N101 | 0.911 (4) | 0.213 (1) | −0.010 (1) | 10.1 (13) |
| N91 | −0.006 (4) | 0.013 (1) | −0.0472 (9) | 6.9 (10) |
| C102 | 0.804 (7) | 0.227 (2) | −0.028 (2) | 17.0 (25) |
| O92 | 0.195 (3) | 0.012 (1) | −0.0740 (8) | 9.2 (10) |
| C95 | −0.138 (6) | −0.008 (2) | −0.029 (1) | 12.5 (19) |
| C93 | 0.083 (5) | −0.062 (2) | −0.040 (1) | 9.7 (16) |
| C103 | 0.702 (6) | 0.239 (2) | −0.048 (1) | 10.7 (16) |
| C96 | −0.037 (7) | 0.067 (2) | −0.055 (2) | 15.5 (23) | wherein the arrangement of the paclitaxel molecules forms solvent sites, the specific dimensions of said solvent sites varying according to the solvent contained therein.

36. An orthorhombic paclitaxel solvate crystal containing a solvent, which is characterized by unit cell parameters a of about 9.51 Å, b of about 27.79 Å, and c of about 34.79 Å; and a space group symmetry p $2_1\ 2_1\ 2_1$; the crystal consisting of eight paclitaxel molecules in an arrangement and conformations according to the fractional atomic coordinates expressed in Table 1;

TABLE 1

| Atom | X | Y | Z | B(A2) |
|---|---|---|---|---|
| C44 | 0.219 (3) | 0.0264 (9) | 0.2022 (7) | 1.2 (7) |
| C41 | 0.517 (3) | 0.092 (1) | 0.1537 (7) | 1.6 (7) |
| C48 | 0.384 (3) | 0.072 (1) | 0.2427 (7) | 1.9 (7) |
| C55 | 0.653 (4) | 0.108 (1) | 0.1774 (8) | 2.3 (8) |
| C51 | 0.681 (4) | 0.063 (1) | 0.2022 (9) | 3.4 (9) |
| C62 | 0.098 (4) | 0.099 (1) | 0.1032 (8) | 3.6 (9) |
| C52' | 0.573 (3) | −0.076 (1) | 0.0594 (7) | 1.7 (7) |
| C49 | 0.526 (4) | 0.098 (1) | 0.2529 (8) | 2.1 (8) |
| C61 | 0.198 (4) | 0.115 (1) | 0.1297 (8) | 2.4 (8) |
| C41' | 0.758 (4) | −0.058 (1) | 0.1229 (8) | 2.7 (8) |
| C45' | 0.768 (5) | −0.172 (1) | 0.038 (1) | 7.9 (14) |
| C52 | 0.701 (3) | 0.0231 (9) | 0.1857 (7) | 1.1 (7) |
| C68 | 0.295 (4) | −0.050 (1) | 0.1792 (8) | 2.1 (8) |
| C70 | 0.840 (4) | 0.088 (1) | 0.287 (1) | 5.6 (11) |
| C43 | 0.368 (3) | 0.0519 (9) | 0.2045 (7) | 0.5 (6) |
| C50 | 0.665 (3) | 0.071 (1) | 0.2403 (8) | 2.1 (8) |
| C42 | 0.368 (3) | 0.0920 (9) | 0.1747 (7) | 0.4 (6) |
| C43' | 0.689 (3) | −0.1076 (9) | 0.0705 (7) | 0.9 (7) |
| C53 | 0.687 (3) | 0.019 (1) | 0.1454 (8) | 2.4 (8) |
| C45 | 0.157 (3) | 0.005 (1) | 0.2369 (8) | 2.4 (8) |
| C42' | 0.712 (4) | −0.08 (1) | 0.1154 (8) | 2.5 (8) |
| C47 | 0.376 (3) | 0.031 (1) | 0.2696 (8) | 2.1 (7) |
| C63 | 0.087 (4) | 0.049 (1) | 0.0956 (9) | 4.9 (10) |
| C67 | 0.033 (3) | 0.136 (1) | 0.0854 (7) | 1.6 (7) |
| C57' | 0.441 (4) | −0.090 (1) | 0.0602 (9) | 4.8 (10) |
| C53' | 0.613 (4) | −0.031 (1) | 0.046 (1) | 5.8 (11) |
| C64 | −0.020 (4) | 0.036 (1) | 0.0694 (9) | 4.9 (11) |
| C66 | −0.074 (4) | 0.122 (1) | 0.0603 (8) | 3.4 (9) |
| C54' | 0.498 (4) | 0.001 (1) | 0.0377 (8) | 2.6 (8) |
| C56' | 0.334 (4) | −0.061 (1) | 0.051 (1) | 5.1 (11) |
| C65 | −0.088 (4) | 0.074 (1) | 0.052 (1) | 5.0 (10) |
| C55' | 0.362 (4) | −0.014 (1) | 0.0372 (8) | 2.7 (8) |
| O44 | 0.235 (2) | −0.0071 (7) | 0.1735 (5) | 2.3 (5) |
| O50 | 0.779 (2) | 0.0972 (7) | 0.2539 (5) | 3.3 (5) |
| O42 | 0.277 (2) | 0.0788 (6) | 0.1461 (4) | 1.0 (4) |
| O53 | 0.646 (2) | −0.0335 (6) | 0.1366 (5) | 1.8 (5) |
| O45 | 0.036 (2) | 0.0369 (7) | 0.2317 (5) | 3.4 (6) |
| O49 | 0.544 (2) | 0.1271 (8) | 0.2745 (5) | 3.5 (6) |

TABLE 1-continued

| Atom | X | Y | Z | B(A2) |
|---|---|---|---|---|
| O61 | 0.211 (2) | 0.1540 (6) | 0.1434 (5) | 1.0 (4) |
| O41' | 0.872 (3) | −0.0418 (7) | 0.1206 (6) | 3.9 (6) |
| O45' | 0.855 (3) | −0.156 (1) | 0.0227 (7) | 8.6 (9) |
| O68 | 0.359 (2) | −0.0540 (7) | 0.2077 (5) | 3.3 (6) |
| O70 | 0.802 (3) | 0.0504 (8) | 0.2991 (6) | 5.1 (7) |
| N44' | 0.669 (3) | −0.1571 (9) | 0.0608 (7) | 3.5 (7) |
| C54 | 0.553 (3) | 0.0428 (9) | 0.1321 (7) | 0.7 (7) |
| C46 | 0.229 (4) | 0.010 (1) | 0.2720 (8) | 2.5 (8) |
| C60 | 0.084 (4) | 0.053 (1) | 0.1934 (8) | 3.0 (9) |
| O41 | 0.494 (2) | 0.1261 (6) | 0.1247 (5) | 1.2 (4) |
| O42' | 0.824 (2) | −0.1385 (7) | 0.1229 (5) | 2.5 (5) |
| O47 | 0.415 (2) | 0.0416 (7) | 0.3046 (5) | 2.6 (5) |
| C59 | 0.275 (4) | 0.113 (1) | 0.2549 (8) | 3.1 (9) |
| C56 | 0.615 (3) | 0.1548 (9) | 0.1965 (7) | 0.8 (7) |
| C57 | 0.788 (3) | 0.117 (1) | 0.1527 (7) | 1.5 (7) |
| C58 | 0.734 (3) | −0.023 (1) | 0.2075 (8) | 2.5 (8) |
| C69 | 0.298 (3) | −0.083 (1) | 0.1483 (8) | 2.2 (8) |
| C71 | 0.950 (4) | 0.120 (1) | 0.2981 (8) | 3.0 (8) |
| C4 | 0.946 (3) | 0.161 (1) | −0.2152 (8) | 2.0 (8) |
| C1 | 0.631 (3) | 0.2169 (9) | −0.1612 (7) | 1.1 (7) |
| C8 | 0.780 (4) | 0.212 (1) | −0.2543 (8) | 2.7 (8) |
| C15 | 0.508 (3) | 0.238 (1) | −0.1862 (8) | 1.7 (7) |
| C11 | 0.474 (4) | 0.199 (1) | −0.2140 (9) | 3.9 (9) |
| C22 | 1.052 (3) | 0.225 (1) | −0.1124 (7) | 1.1 (7) |
| C6' | 0.473 (3) | 0.099 (1) | −0.0287 (8) | 2.1 (8) |
| C12' | 0.573 (3) | −0.032 (1) | −0.0938 (8) | 2.5 (8) |
| C9 | 0.642 (4) | 0.235 (1) | −0.2626 (8) | 2.7 (8) |
| C21 | 0.953 (4) | 0.240 (1) | −0.1397 (8) | 3.2 (9) |
| C1' | 0.386 (3) | 0.0635 (9) | −0.1493 (7) | 0.6 (6) |
| C5' | 0.545 (4) | 0.075 (1) | −0.0630 (9) | 4.7 (10) |
| C12 | 0.466 (3) | 0.1535 (9) | −0.2038 (7) | 1.0 |
| C28 | 0.850 (4) | 0.080 (1) | −0.1952 (8) | 3.2 (9) |
| C30 | 0.325 (4) | 0.236 (1) | −0.301 (1) | 4.8 (10) |
| C3 | 0.788 (3) | 0.1857 (9) | −0.2161 (7) | 0.6 (6) |
| C10 | 0.491 (3) | 0.207 (1) | −0.2537 (7) | 1.7 (7) |
| C2 | 0.770 (4) | 0.222 (1) | −0.1823 (8) | 2.5 (8) |
| C3' | 0.535 (4) | 0.019 (1) | −0.1081 (8) | 2.3 (8) |
| C13 | 0.466 (3) | 0.1421 (9) | −0.1625 (7) | 1.0 |
| C5 | 1.011 (3) | 0.139 (1) | −0.2506 (8) | 2.4 (8) |
| C2' | 0.444 (3) | 0.014 (1) | −0.1411 (8) | 2.1 (8) |
| C7 | 0.787 (3) | 0.171 (1) | −0.2825 (8) | 2.0 (8) |
| C23 | 1.082 (3) | 0.175 (1) | −0.1095 (7) | 1.3 (7) |
| C27 | 1.134 (3) | 0.258 (1) | −0.0928 (8) | 2.0 (7) |
| C11' | 0.572 (4) | 0.127 (1) | −0.0072 (9) | 5.0 (10) |
| C7' | 0.342 (4) | 0.091 (1) | −0.0169 (8) | 3.3 (9) |
| C17' | 0.525 (4) | −0.049 (1) | −0.0606 (9) | 4.2 (10) |
| C13' | 0.657 (5) | −0.059 (1) | −0.114 (1) | 6.8 (12) |
| C26 | 1.238 (4) | 0.245 (1) | −0.0687 (8) | 3.0 (8) |
| C24 | 1.192 (4) | 0.162 (1) | −0.0871 (9) | 3.9 (10) |
| C8' | 0.286 (4) | 0.110 (1) | 0.0165 (9) | 4.3 (10) |
| C10' | 0.530 (5) | 0.142 (1) | 0.027 (1) | 7.1 (12) |
| C16' | 0.564 (4) | −0.091 (1) | −0.0481 (9) | 5.1 (11) |
| C14' | 0.697 (4) | −0.104 (1) | −0.1009 (9) | 5.2 (11) |
| C25 | 1.264 (4) | 0.195 (1) | −0.0635 (9) | 3.8 (9) |
| C9' | 0.393 (4) | 0.137 (1) | 0.0367 (9) | 3.9 (9) |
| C15' | 0.650 (4) | −0.120 (1) | −0.0677 (9) | 5.1 (11) |
| O4 | 0.923 (2) | 0.1233 (7) | −0.1868 (5) | 1.9 (5) |
| O10 | 0.380 (2) | 0.2383 (7) | −0.2634 (5) | 3.0 (5) |
| O2 | 0.880 (2) | 0.2052 (6) | −0.1559 (5) | 1.5 (4) |
| O13 | 0.503 (2) | 0.0934 (7) | −0.1594 (5) | 2.7 (5) |
| O5 | 1.122 (2) | 0.1722 (7) | −0.2426 (5) | 2.7 (5) |
| O9 | 0.629 (2) | 0.2698 (6) | −0.2812 (5) | 1.4 (4) |
| O21 | 0.930 (2) | 0.2810 (7) | −0.1445 (5) | 2.2 (5) |
| O1' | 0.272 (2) | 0.0783 (7) | −0.1498 (5) | 3.2 (5) |
| O5' | 0.665 (3) | 0.0900 (8) | −0.0721 (6) | 4.1 (6) |
| O28 | 0.791 (2) | 0.0807 (7) | −0.2238 (5) | 3.2 (6) |
| O30 | 0.371 (3) | 0.2020 (9) | −0.3153 (6) | 5.9 (7) |
| N4' | 0.460 (3) | 0.0444 (8) | −0.0782 (6) | 1.5 (6) |
| C14 | 0.599 (3) | 0.165 (1) | −0.1470 (7) | 1.5 (7) |
| C6 | 0.947 (4) | 0.151 (1) | −0.2854 (8) | 2.9 (9) |
| C20 | 1.078 (3) | 0.188 (1) | −0.2072 (7) | 1.9 (8) |
| O1 | 0.648 (2) | 0.2464 (6) | −0.1304 (5) | 1.3 (4) |
| O2' | 0.324 (2) | −0.0158 (7) | −0.1374 (5) | 2.5 (5) |
| O7 | 0.742 (2) | 0.1856 (6) | −0.3173 (5) | 1.9 (5) |
| C19 | 0.891 (3) | 0.253 (1) | −0.2590 (7) | 1.6 (7) |
| C16 | 0.543 (3) | 0.287 (1) | −0.2021 (7) | 1.3 (7) |
| C17 | 0.369 (3) | 0.243 (1) | −0.1634 (7) | 1.4 (7) |
| C18 | 0.433 (3) | 0.113 (1) | −0.2291 (7) | 1.3 (7) |
| C29 | 0.868 (4) | 0.047 (1) | −0.1660 (8) | 2.9 (8) |
| C31 | 0.216 (4) | 0.271 (1) | −0.3066 (9) | 3.6 (9) |
| O112 | 0.185 (4) | −0.202 (1) | 0.1087 (8) | 10.1 (10) |
| O113 | 0.068 (4) | −0.130 (1) | 0.0768 (9) | 13.4 (12) |
| O111 | 0.465 (3) | −0.1962 (9) | 0.1084 (7) | 6.9 (8) |
| C92 | 0.104 (4) | −0.013 (1) | −0.057 (1) | 6.5 (12) |
| C94 | −0.058 (6) | −0.051 (2) | −0.021 (1) | 10.1 (16) |
| N101 | 0.911 (4) | 0.213 (1) | −0.010 (1) | 10.1 (13) |
| N91 | −0.006 (4) | 0.013 (1) | −0.0472 (9) | 6.9 (10) |
| C102 | 0.804 (7) | 0.227 (2) | −0.028 (2) | 17.0 (25) |
| O92 | 0.195 (3) | 0.012 (1) | −0.0740 (8) | 9.2 (10) |
| C95 | −0.138 (6) | −0.008 (2) | −0.029 (1) | 12.5 (19) |
| C93 | 0.083 (5) | −0.062 (2) | −0.040 (1) | 9.7 (16) |
| C103 | 0.702 (6) | 0.239 (2) | −0.048 (1) | 10.7 (16) |
| C96 | −0.037 (7) | 0.067 (2) | −0.055 (2) | 15.5 (23) | wherein the arrangement of the paclitaxel molecules forms solvent sites, the specific dimensions of said solvent sites varying according to the solvent contained therein.

\* \* \* \* \*

UNITED STATES PATENT AND TRADEMARK OFFICE
CERTIFICATE OF CORRECTION

PATENT NO. : 6,858,644 B2
DATED : February 22, 2005
INVENTOR(S) : Benigni et al.

It is certified that error appears in the above-identified patent and that said Letters Patent is hereby corrected as shown below:

<u>Column 16,</u>
Line 48, after "pyrimidinone" delete "and".
Line 49, delete "alos" and enter -- also --.

<u>Column 17,</u>
Line 38, after "pyrimidinone" delete "and".

Signed and Sealed this

Seventh Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,858,644 B2
APPLICATION NO. : 10/304615
DATED : February 22, 2005
INVENTOR(S) : Benigni et al.

It is certified that error appears in the above-identified patent and that said Letters Patent is hereby corrected as shown below:

In Column 20, the Table in Claim 36 should read:

TABLE 3

| Atom | X | Y | Z |
|---|---|---|---|
| C15 | 0.5181( 7) | 0.4318(2) | -0.1705(2) |
| C17 | 0.3753( 8) | 0.4393(2) | -0.1463(2) |
| C22 | 1.0541( 8) | 0.4133(3) | -0.0894(2) |
| C24 | 1.1654(15) | 0.3472(5) | -0.0555(4) |
| C26 | 1.2480(12) | 0.4297(5) | -0.0452(3) |
| C27 | 1.1484( 9) | 0.4461(3) | -0.0704(2) |
| C31 | 0.2362(10) | 0.4605(4) | -0.3026(3) |
| C1' | 0.3882(12) | 0.2588(3) | -0.1313(2) |
| O1' | 0.2716( 8) | 0.2748(2) | -0.1316(2) |
| O5' | 0.7170( 6) | 0.2745(2) | -0.0631(2) |
| N4' | 0.5110( 7) | 0.2340(2) | -0.0591(2) |

UNITED STATES PATENT AND TRADEMARK OFFICE
CERTIFICATE OF CORRECTION

PATENT NO. : 6,858,644 B2
APPLICATION NO. : 10/304615
DATED : February 22, 2005
INVENTOR(S) : Benigni et al.

It is certified that error appears in the above-identified patent and that said Letters Patent is hereby corrected as shown below:

| | | | |
|---|---|---|---|
| C5' | 0.6083(10) | 0.2668(3) | -0.0462(2) |
| C6' | 0.5634( 8) | 0.2947(3) | -0.0108(2) |
| C17' | 0.6503(14) | 0.1250(4) | -0.1024(3) |
| C10' | 0.6185(12) | 0.3619(3) | 0.0302(3) |
| C7' | 0.4637(11) | 0.2814(3) | 0.0139(3) |
| C3' | 0.5409(10) | 0.2035(3) | -0.0918(2) |
| C12' | 0.5667(10) | 0.1506(3) | -0.0801(3) |
| O10 | 0.3932( 5) | 0.4342(2) | -0.2556(2) |
| C19 | 0.9021( 8) | 0.4486(3) | -0.2460(2) |
| C7 | 0.8025( 8) | 0.3678(3) | -0.2726(2) |
| O7 | 0.7601( 6) | 0.3836(2) | -0.3087(2) |
| O28 | 0.8041( 7) | 0.2715(2) | -0.2104(2) |
| C23 | 1.0637(10) | 0.3650(4) | -0.0819(3) |
| C25 | 1.2601(12) | 0.3811(5) | -0.0379(3) |

UNITED STATES PATENT AND TRADEMARK OFFICE
CERTIFICATE OF CORRECTION

PATENT NO. : 6,858,644 B2
APPLICATION NO. : 10/304615
DATED : February 22, 2005
INVENTOR(S) : Benigni et al.

It is certified that error appears in the above-identified patent and that said Letters Patent is hereby corrected as shown below:

| | | | |
|---|---|---|---|
| C11' | 0.6469(11) | 0.3348(3) | -0.0048(3) |
| C15' | 0.6177(20) | 0.0558(4) | -0.0623(6) |
| C9' | 0.5143(13) | 0.3473(4) | 0.0541(3) |
| C14' | 0.5250(18) | 0.0826(5) | -0.0367(4) |
| C8' | 0.4355(11) | 0.3099(4) | 0.0462(3) |
| C16' | 0.6829(16) | 0.0731(5) | -0.0929(4) |
| C16 | 0.5505(7) | 0.4826(2) | -0.1869(2) |
| O1 | 0.6465(4) | 0.4443(1) | -0.1114(1) |
| C1 | 0.6357(7) | 0.4131(2) | -0.1438(2) |
| O9 | 0.6431(6) | 0.4677(2) | -0.2716(2) |
| C9 | 0.6469(8) | 0.4316(3) | -0.2514(2) |
| O2 | 0.8821(4) | 0.4002(1) | -0.1358(1) |
| C21 | 0.9594(7) | 0.4337(3) | -0.1179(2) |
| C2 | 0.7825(6) | 0.4155(2) | -0.1648(2) |

UNITED STATES PATENT AND TRADEMARK OFFICE
CERTIFICATE OF CORRECTION

PATENT NO. : 6,858,644 B2
APPLICATION NO. : 10/304615
DATED : February 22, 2005
INVENTOR(S) : Benigni et al.

It is certified that error appears in the above-identified patent and that said Letters Patent is hereby corrected as shown below:

| | | | |
|---|---|---|---|
| C28 | 0.8611( 9) | 0.2745(3) | -0.1803(3) |
| C29 | 0.8698(11) | 0.2383(3) | -0.1500(3) |
| O13 | 0.5052( 5) | 0.2848(1) | -0.1402(1) |
| C2' | 0.4244(10) | 0.2070(3) | -0.1223(2) |
| O2' | 0.3007( 7) | 0.1845(2) | -0.1076(2) |
| C18 | 0.4370( 8) | 0.3070(2) | -0.2168(2) |
| O30 | 0.4016(10) | 0.3983(3) | -0.3114(2) |
| C30 | 0.3435(10) | 0.4274(4) | -0.2923(3) |
| C10 | 0.5059( 8) | 0.4050(2) | -0.2426(2) |
| C11 | 0.4893( 7) | 0.3932(2) | -0.2004(2) |
| C12 | 0.4714( 8) | 0.3461(3) | -0.1898(3) |
| C13 | 0.4820( 8) | 0.3357(2) | -0.1475(2) |
| C14 | 0.6040( 7) | 0.3628(2) | -0.1278(2) |
| C8 | 0.7913( 7) | 0.4089(2) | -0.2405(2) |

UNITED STATES PATENT AND TRADEMARK OFFICE
CERTIFICATE OF CORRECTION

PATENT NO.       : 6,858,644 B2
APPLICATION NO.  : 10/304615
DATED            : February 22, 2005
INVENTOR(S)      : Benigni et al.

It is certified that error appears in the above-identified patent and that said Letters Patent is hereby corrected as shown below:

| | | | |
|---|---|---|---|
| C3   | 0.8009( 6) | 0.3818(2) | -0.2020(2) |
| O21  | 0.9509( 5) | 0.4761(2) | -0.1253(1) |
| O4   | 0.9252( 5) | 0.3149(2) | -0.1704(2) |
| C6   | 0.9464( 8) | 0.3465(3) | -0.2752(2) |
| O5   | 1.1373( 5) | 0.3679(2) | -0.2279(2) |
| C4   | 0.9412( 8) | 0.3531(2) | -0.1991(2) |
| C20  | 1.0812( 8) | 0.3794(3) | -0.1906(2) |
| C5   | 1.0144( 9) | 0.3344(3) | -0.2356(2) |
| C13' | 0.5806(13) | 0.1304(4) | -0.0474(3) |
| C43  | 0.8809( 6) | 0.6438(2) | -0.2016(2) |
| C45  | 0.6695( 8) | 0.6906(3) | -0.2388(2) |
| C46  | 0.7522( 9) | 0.6828(3) | -0.2765(2) |
| C49  | 1.0427( 8) | 0.5963(3) | -0.2512(2) |
| C55  | 1.1585( 7) | 0.5926(2) | -0.1670(2) |

Page 5 of 10

UNITED STATES PATENT AND TRADEMARK OFFICE
CERTIFICATE OF CORRECTION

PATENT NO. : 6,858,644 B2
APPLICATION NO. : 10/304615
DATED : February 22, 2005
INVENTOR(S) : Benigni et al.

Page 6 of 10

It is certified that error appears in the above-identified patent and that said Letters Patent is hereby corrected as shown below:

| | | | |
|---|---|---|---|
| C57 | 1.2951( 7) | 0.5844(2) | -0.1420(2) |
| C58 | 1.2564( 7) | 0.7179(2) | -0.2092(2) |
| C60 | 0.5978( 7) | 0.6441(3) | -0.1949(3) |
| C66 | 0.4412( 9) | 0.5914(3) | -0.0428(2) |
| C65 | 0.4404( 9) | 0.6411(4) | -0.0324(2) |
| C64 | 0.5279(11) | 0.6739(3) | -0.0507(3) |
| C69 | 0.7927(10) | 0.7875(3) | -0.1509(3) |
| C71 | 1.4484( 9) | 0.5682(3) | -0.3008(3) |
| C41' | 1.2782(11) | 0.7650(3) | -0.1241(2) |
| C43' | 1.2300( 9) | 0.8180(2) | -0.0692(2) |
| O49 | 1.0493( 5) | 0.5605(2) | -0.2704(2) |
| C55' | 1.0693(13) | 0.7061(3) | -0.0234(3) |
| C52' | 1.1217(10) | 0.7833(2) | -0.0531(2) |
| N44' | 1.1992( 8) | 0.8670(2) | -0.0558(2) |

UNITED STATES PATENT AND TRADEMARK OFFICE
CERTIFICATE OF CORRECTION

PATENT NO. : 6,858,644 B2
APPLICATION NO. : 10/304615
DATED : February 22, 2005
INVENTOR(S) : Benigni et al.

It is certified that error appears in the above-identified patent and that said Letters Patent is hereby corrected as shown below:

| | | | |
|---|---|---|---|
| C45' | 1.2893(13) | 0.8950(4) | -0.0356(3) |
| C57' | 1.1634(10) | 0.7394(3) | -0.0371(2) |
| C54' | 0.8780(10) | 0.7566(3) | -0.0457(3) |
| C42 | 0.8925(7) | 0.6088(2) | -0.1656(2) |
| O45' | 0.5524(5) | 0.6576(2) | -0.2341(2) |
| O47 | 0.9403(6) | 0.6458(2) | -0.3093(2) |
| C47 | 0.8936(9) | 0.6621(3) | -0.2714(2) |
| O50 | 1.2954(5) | 0.5937(2) | -0.2519(2) |
| C70 | 1.3318(10) | 0.5990(3) | -0.2876(3) |
| C63 | 0.6178(8) | 0.6576(3) | -0.0799(2) |
| C59 | 0.7854(8) | 0.5800(3) | -0.2514(2) |
| C44 | 0.7370(8) | 0.6727(2) | -0.1996(2) |
| O68 | 0.8736(7) | 0.7538(2) | -0.2102(2) |
| O41' | 1.3962(8) | 0.7494(2) | -0.1225(2) |

UNITED STATES PATENT AND TRADEMARK OFFICE
CERTIFICATE OF CORRECTION

PATENT NO. : 6,858,644 B2
APPLICATION NO. : 10/304615
DATED : February 22, 2005
INVENTOR(S) : Benigni et al.

It is certified that error appears in the above-identified patent and that said Letters Patent is hereby corrected as shown below:

| | | | |
|---|---|---|---|
| C49' | 1.1713(20) | 1.0251(4) | 0.0158(4) |
| C48' | 1.0938(17) | 1.0081(4) | -0.0154(4) |
| C53' | 0.9795(11) | 0.7921(3) | -0.0585(3) |
| C47' | 1.1375(15) | 0.9632(3) | -0.0334(3) |
| C50' | 1.2853(17) | 0.9993(5) | 0.0295(4) |
| C55' | 0.9280(14) | 0.7160(3) | -0.0286(3) |
| C51' | 1.3239(12) | 0.9565(4) | 0.0107(3) |
| C61 | 0.7121( 7) | 0.5880(2) | -0.1203(2) |
| O61 | 0.7200( 5) | 0.5470(2) | -0.1292(1) |
| C62 | 0.6189( 7) | 0.6081(3) | -0.0889(2) |
| C67 | 0.5324( 8) | 0.5741(3) | -0.0706(2) |
| O42 | 0.7871( 5) | 0.6235(1) | -0.1381(1) |
| O44 | 0.7456( 5) | 0.7085(2) | -0.1714(1) |
| C68 | 0.8102( 9) | 0.7497(3) | -0.1803(3) |

UNITED STATES PATENT AND TRADEMARK OFFICE
CERTIFICATE OF CORRECTION

PATENT NO. : 6,858,644 B2
APPLICATION NO. : 10/304615
DATED : February 22, 2005
INVENTOR(S) : Benigni et al.

It is certified that error appears in the above-identified patent and that said Letters Patent is hereby corrected as shown below:

| | | | |
|---|---|---|---|
| C42' | 1.2378( 9) | 0.8158(2) | -0.1127(2) |
| O42' | 1.3458( 7) | 0.8475(2) | -0.1253(2) |
| C52 | 1.2129( 7) | 0.6778(2) | -0.1834(2) |
| C53 | 1.1895( 7) | 0.6875(2) | -0.1418(2) |
| O53 | 1.1648( 5) | 0.7385(1) | -0.1348(1) |
| C54 | 1.0635( 7) | 0.6614(2) | -0.1257(2) |
| C41 | 1.0334( 6) | 0.6107(2) | -0.1430(2) |
| C51 | 1.1903( 7) | 0.6320(2) | -0.1965(2) |
| O41 | 1.0162( 4) | 0.5785(1) | -0.1105(1) |
| C56 | 1.1285( 7) | 0.5428(2) | -0.1855(2) |
| C50 | 1.1793( 8) | 0.6218(2) | -0.2389(2) |
| O70 | 1.2637(12) | 0.6259(3) | -0.3085(3) |
| O45 | 1.4073(13) | 0.8794(2) | -0.0307(2) |
| C46' | 1.2515(13) | 0.9385(3) | -0.0202(2) |

UNITED STATES PATENT AND TRADEMARK OFFICE
CERTIFICATE OF CORRECTION

PATENT NO. : 6,858,644 B2
APPLICATION NO. : 10/304615
DATED : February 22, 2005
INVENTOR(S) : Benigni et al.

It is certified that error appears in the above-identified patent and that said Letters Patent is hereby corrected as shown below:

| C48  | 0.8968( 7)  | 0.6188(2) | -0.2423(2) |
| ---- | ----------- | --------- | ---------- |
| N125 | 0.7714(10)  | 0.5174(3) | -0.3682(3) |
| C126 | 0.7315(13)  | 0.5631(5) | -0.3764(4) |
| C127 | 0.8863(16)  | 0.5059(5) | -0.3584(4) |
| C128 | 0.6543(13)  | 0.4804(4) | -0.3756(4) |
| O131 | 0.9302( 9)  | 0.9017(3) | -0.0990(3) |
| O132 | 0.6429(16)  | 0.9026(5) | -0.0976(4) |
| O129 | 0.9125( 9)  | 0.4519(3) | -0.3483(3) |
| O130 | 0.7787(23)  | 0.6069(8) | -0.3632(7) |

Signed and Sealed this

Eighteenth Day of March, 2008

JON W. DUDAS
*Director of the United States Patent and Trademark Office*